United States Patent
Miao et al.

(10) Patent No.: US 10,758,540 B2
(45) Date of Patent: Sep. 1, 2020

(54) TREATMENT OF FOCAL SEGMENTAL GLOMERULOSCLEROSIS WITH CCR2 ANTAGONISTS

(71) Applicant: CHEMOCENTRYX, INC., Mountain View, CA (US)

(72) Inventors: Zhenhua Miao, Mountain View, CA (US); Thomas J. Schall, Mountain View, CA (US); Rajinder Singh, Belmont, CA (US)

(73) Assignee: ChemoCentryx, Inc., Mountain View, CA (US)

( * ) Notice: Subject to any disclaimer, the term of this patent is extended or adjusted under 35 U.S.C. 154(b) by 0 days.

(21) Appl. No.: 16/156,608

(22) Filed: Oct. 10, 2018

(65) Prior Publication Data
US 2019/0134042 A1 May 9, 2019

Related U.S. Application Data

(60) Provisional application No. 62/570,778, filed on Oct. 11, 2017.

(51) Int. Cl.
| | | |
|---|---|---|
| *A61K 31/437* | (2006.01) | |
| *A61K 31/519* | (2006.01) | |
| *A61K 31/422* | (2006.01) | |
| *A61K 31/41* | (2006.01) | |
| *A61P 13/12* | (2006.01) | |

(52) U.S. Cl.
CPC .......... *A61K 31/519* (2013.01); *A61K 31/41* (2013.01); *A61K 31/422* (2013.01); *A61K 31/437* (2013.01); *A61P 13/12* (2018.01)

(58) Field of Classification Search
CPC .. A61K 31/437; A61K 31/519; C07D 471/04; C07D 487/04
USPC ............... 514/265.1, 300; 544/280; 546/113
See application file for complete search history.

(56) References Cited

U.S. PATENT DOCUMENTS

| | | |
|---|---|---|
| 3,817,837 A | 6/1974 | Rubenstein et al. |
| 3,850,752 A | 11/1974 | Schuurs et al. |
| 3,901,855 A | 8/1975 | Arnold |
| 3,939,350 A | 2/1976 | Kronick et al. |
| 3,996,345 A | 12/1976 | Ullman et al. |
| 4,166,452 A | 9/1979 | Generales |
| 4,227,437 A | 10/1980 | Inloes et al. |
| 4,256,108 A | 3/1981 | Theeuwes |
| 4,265,874 A | 5/1981 | Bonsen et al. |
| 4,275,149 A | 6/1981 | Litman et al. |
| 4,277,437 A | 7/1981 | Maggio |
| 4,366,241 A | 12/1982 | Tom et al. |
| 4,403,607 A | 9/1983 | Woo et al. |
| 5,120,643 A | 6/1992 | Ching et al. |
| 5,292,758 A | 3/1994 | Yoshino et al. |
| 5,446,139 A | 8/1995 | Seela et al. |
| 5,571,775 A | 11/1996 | Van Heertum et al. |
| 5,780,488 A | 7/1998 | Bergman et al. |
| 5,973,148 A | 10/1999 | Ringer et al. |
| 5,990,479 A | 11/1999 | Weiss et al. |
| 6,207,392 B1 | 3/2001 | Weiss et al. |
| 6,251,303 B1 | 6/2001 | Bawendi et al. |
| 6,306,610 B1 | 10/2001 | Bawendi et al. |
| 6,312,914 B1 | 11/2001 | Kardos et al. |
| 6,319,426 B1 | 11/2001 | Bawendi et al. |
| 6,322,901 B1 | 11/2001 | Bawendi et al. |

(Continued)

FOREIGN PATENT DOCUMENTS

| | | |
|---|---|---|
| DE | 3825041 A1 | 2/1990 |
| EP | 0472053 B1 | 6/1998 |

(Continued)

OTHER PUBLICATIONS

International Search Report and Written Opinion dated Jan. 4, 2019 corresponding to PCT/US2018/055244 filed Oct. 10, 2018 (13 pages).

(Continued)

*Primary Examiner* — Jeffrey H Murray
(74) *Attorney, Agent, or Firm* — Barnes & Thornburg LLP; Ryan L. Marshall; Jonathan M. Hartley

(57) ABSTRACT

Provided herein are methods of treating focal segmental glomerulosclerosis, said methods include administering to a subject in need thereof a therapeutically effective amount of a CCR2 antagonist. In some embodiments, the CCR2 antagonist is used in monotherapy. In some embodiments, the CCR2 antagonist is used in combination therapy. In some embodiments, the additional therapeutic agent is a RAAS blocker and/or an endothelin receptor inhibitor. The CCR2 antagonist may have the structure of formula (I).

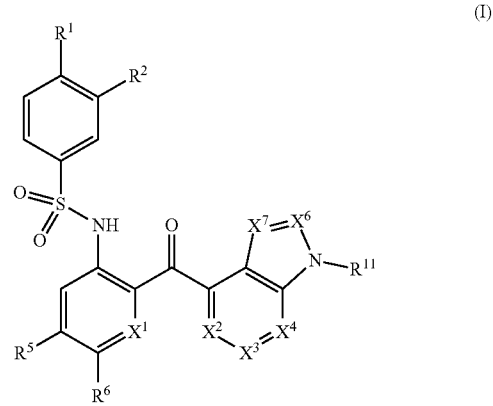

26 Claims, 6 Drawing Sheets

(56) References Cited

U.S. PATENT DOCUMENTS

| | | |
|---|---|---|
| 6,326,144 B1 | 12/2001 | Bawendi et al. |
| 6,380,206 B1 | 4/2002 | Pamukcu et al. |
| 6,403,607 B1 | 6/2002 | Hidaka et al. |
| 6,423,551 B1 | 7/2002 | Weiss et al. |
| 6,444,143 B2 | 9/2002 | Bawendi et al. |
| 6,451,339 B2 | 9/2002 | Patel et al. |
| 6,479,527 B1 | 11/2002 | Barker et al. |
| 6,489,452 B1 | 12/2002 | Tateishi et al. |
| 6,939,885 B2 | 9/2005 | Ungashe et al. |
| 7,282,502 B2 | 10/2007 | Fleming et al. |
| 7,496,807 B2 | 2/2009 | Nagai et al. |
| 7,622,583 B2 | 11/2009 | Ungashe et al. |
| 7,884,110 B2 | 2/2011 | Krasinski et al. |
| 8,093,247 B2 | 1/2012 | Ungashe et al. |
| 8,519,135 B2 | 8/2013 | Chen et al. |
| 8,546,408 B2 | 10/2013 | Krasinski et al. |
| 9,314,450 B2 | 4/2016 | Pfleger et al. |
| 9,394,307 B2 | 7/2016 | Krasinski et al. |
| 9,745,312 B2 | 8/2017 | Krasinski et al. |
| 2002/0052363 A1 | 5/2002 | Dinsmore et al. |
| 2002/0103202 A1 | 8/2002 | Pinto et al. |
| 2003/0229081 A1 | 12/2003 | Maduskuie |
| 2004/0023286 A1 | 2/2004 | Wei |
| 2004/0038976 A1 | 2/2004 | Fleming et al. |
| 2004/0106613 A1 | 6/2004 | McNaughton-Smith et al. |
| 2004/0171654 A1 | 9/2004 | Ugashe et al. |
| 2006/0111351 A1 | 5/2006 | Ungashe et al. |
| 2006/0173019 A1 | 8/2006 | Ungashe et al. |
| 2007/0021466 A1 | 1/2007 | Ungashe et al. |
| 2007/0037794 A1 | 2/2007 | Ungashe et al. |
| 2007/0219245 A1 | 9/2007 | Hou et al. |
| 2009/0197884 A1 | 8/2009 | Ghosh et al. |
| 2010/0056509 A1 | 3/2010 | Ungashe et al. |
| 2010/0234364 A1 | 9/2010 | Basak et al. |
| 2010/0249118 A1 | 9/2010 | Ibrahim et al. |
| 2011/0118248 A1 | 5/2011 | Ungashe et al. |
| 2011/0274696 A1 | 11/2011 | Gladue et al. |
| 2011/0319433 A1 | 12/2011 | Krasinski et al. |
| 2012/0122860 A1 | 5/2012 | Visor et al. |
| 2013/0210149 A1 | 8/2013 | Li et al. |
| 2013/0252951 A1 | 9/2013 | Boyd et al. |
| 2014/0031348 A1 | 1/2014 | Ungashe et al. |
| 2014/0100237 A1 | 4/2014 | Krasinski et al. |
| 2014/0235661 A1 | 8/2014 | Ebel et al. |
| 2015/0080351 A1 | 3/2015 | Ungashe et al. |
| 2017/0095458 A1 | 4/2017 | Ungashe et al. |
| 2017/0334920 A1 | 11/2017 | Krasinski et al. |
| 2017/0368043 A1 | 12/2017 | Bekker et al. |

FOREIGN PATENT DOCUMENTS

| | | |
|---|---|---|
| EP | 0937711 A1 | 8/1999 |
| EP | 1334719 A2 | 8/2003 |
| JP | 51113060 A2 | 5/1986 |
| JP | 1364168 A2 | 12/1992 |
| JP | 6135934 A2 | 5/1994 |
| JP | 6145145 A2 | 5/1994 |
| JP | 2000159665 A2 | 6/2000 |
| JP | 2001089412 A2 | 4/2001 |
| JP | 2003040726 A2 | 2/2003 |
| WO | 9420142 A1 | 9/1994 |
| WO | 9811218 A1 | 3/1998 |
| WO | 9942439 A1 | 8/1999 |
| WO | 00040560 A1 | 7/2000 |
| WO | 0100611 A1 | 1/2001 |
| WO | 0102369 A2 | 1/2001 |
| WO | 0172744 A1 | 10/2001 |
| WO | 02101350 A2 | 12/2002 |
| WO | 03032994 A2 | 4/2003 |
| WO | 03051870 A1 | 6/2003 |
| WO | 03099773 A1 | 12/2003 |
| WO | 04046092 A2 | 6/2004 |
| WO | 04056774 A2 | 7/2004 |
| WO | 04058164 A2 | 7/2004 |
| WO | 04058265 A1 | 7/2004 |
| WO | 04085384 A2 | 10/2004 |
| WO | 04099127 A1 | 11/2004 |
| WO | 04105794 A2 | 12/2004 |
| WO | 05004810 A2 | 1/2005 |
| WO | 05028445 A2 | 3/2005 |
| WO | 05112916 A2 | 12/2005 |
| WO | 05112925 A1 | 12/2005 |
| WO | 06076644 A2 | 7/2006 |
| WO | 07014008 A2 | 2/2007 |
| WO | 07014054 A2 | 2/2007 |
| WO | 2008/008431 A2 | 1/2008 |
| WO | 2008/008431 A3 | 1/2008 |
| WO | 08008374 A2 | 1/2008 |
| WO | 08008394 A1 | 1/2008 |
| WO | 08008431 A2 | 1/2008 |
| WO | 09009740 A1 | 1/2009 |
| WO | 2016/187393 A1 | 11/2016 |
| WO | 2018/098353 A1 | 5/2018 |

OTHER PUBLICATIONS

Miao, Zhenhua et al., "CCR2 Antagonism Reduces Proteinuria and Glomerular Injury in Murine Models of Focal Segmental Glomerulosclerosis (FSGS)," *Nephrology Dialysis Transplantation* (May 26, 2019); 32(suppl-3):iii97, https://doi.org/10.1093/ndt/gfx134 + 6 pages.

Kavanaugh, et al., "Role of CD11/CD18 in Adhesion and Transendothelial Migration of T Cells", J. Immunol., 146:4149-4156 (Jun. 1991).

Kitagawa, et al., "Blockade of CCR2 Ameliorates Progressive Fibrosis in Kidney", American Journal of Pathology, 165(1):237-246 (Jul. 2004).

Kontoyiannis et al., "Impaired on/Off Regulation of TNF Biosynthesis in Mice Lacking TNF AU-Rich Elements: Implications for Joint and Gut-Associated Immunopathologies", Immunity, 10:387-398 (Mar. 1999).

Kontoyiannis, et al., "Genetic Dissection of the Cellular Pathways and Signaling Mechanisms in Modeled Tumor Necrosis Factor-induced Crohn's-like Inflammatory Bowel Disease," J. Exp. Med., 196(2):1563-1574 (2002).

Kosiewicz, et al., "Th1-type responses mediate spontaneous ileitis in a novel murine model of Crohn's disease", J. 21in. Invest., 107(6):695-702 (Mar. 2001).

Kunkel, et al., "Lymphocyte CC Chemokine Receptor 9 and Epithelial Thymus-expressed Chemokine (TECK) Expression Distinguish the Small Intestinal Immune Compartment: Epithelial Expression of Tissue-specific chemokines as an Organizing Prindiple in Regional Immunity", J. Exp. Med., 192(5):761-777 (Sep. 2000).

Kuse, Masaki, et al., "Novel synthetic route of aryl-aminopyrazine," Tetrahedron, 60:835-840 (2004).

Llyod, et al., "Rantes and Monocyte Chemoattractant Protein-1 (MCP-1) Play an Important Role in the nflammatory Phase of Crescentic Nephritis, but Only Mcp-1 Is Involved in Crescent Formation and Interstitial 7ibrosis", J. Exp. Med., 185(7):1371-1380 (Apr. 1997).

Martins, et al., "Nanoparticle Drug Delivery Systems: Recent Patents and Applications in Nanomedicine," Recent Patents on Nanomedicine, 3(2):105-118 (2013).

Mine et al "Increased expression levels of monocyte CCR2 and monocyte chemoattractant protein-1 in patients with liabetes mellitus", Biochemical and Biophysical Research Comm., 334:780-785 (2006).

Morii, et al., "Association of monocyte chemoattractant protein-1 with renal tubular damage in diabetic nephropathy", Journal of Diabetes Complications, 17:11-15 (2003).

Murphy, "The Molecular Biology of Leukocyte Chemoattractant Receptors", Ann. Rev. Immun., 12:593-633 (1994).

Neote, et al., "Molecular Cloning, Functional Expression, and Signaling characteristics of a C-C Chemokine Receptor", Cell, 72:415-425 (Feb. 1993).

Ogata, et al., "The Role of Monocyte Chemoattractant Protein-1 (MCP-1) in the Pathogenesis of Collagen-Induced Arthritis in Rats", Journal of Pathology, 182:106-114 (1997).

(56) References Cited

OTHER PUBLICATIONS

Panwala, et al., "A Novel Model of Inflammatory Bowel Disease: Mice Deficient for the Multiple Drug Resistance Gene, mdrla, Spontaneously Develop Colitis", J. Immunol., 161:5733-5744 (1998).
Papadakis, et al., "The Role of Thymus-Expressed Chemokine and Its Receptor CCR9 on Lymphocytes in the Regional Specialization of the Mucosal Immune System", J. Immunol., 165:5069-5076 (2000).
Papadakis, et al., "CCR9-Positive Lymphocytes and Thymus-Expressed Chemokine Distinguish Small Bowel from Colonic Crohn's Disease," Gastroenterology, 121(2):248-254 (2001).
Plater-Zyberk, et al., "Effect of a CC chemokine receptor antagonist on collagen induced arthritis in DBA/1 mice", Immunology Letters, 57:117-120 (1997).
Powrie et al., "Phenotypically distinct subsets of CD4+ T cells induce or protect from chronic intestinal inflammation in C. B-17 scid mice", Int. Immunol., 5(11)1461-1471 (1993).
Qiuping, et al., "Selectively Increased Expression and Functions of Chemokine Receptor CCR9 on CD4+ T Cells from Patients with T-Cell Lineage Acute Lymphocytic Leukemia", Cancer Res., 63:6469-6477 (Oct. 2003).
Rivera-Nieves, et al., "Antibody Blockade of CCL25/CCR9 Ameliorates Early but not Late Chronic Murine Ileitis," Gastroenterology, 131(5):1518-1529 (2006).
Sartipy, et al., "Monocyte chemoattractant protein 1 in obesity and insulin resistance", PNAS, 100(12):7265-7270 (Jun. 2003).
Scaife, et al., "Detection of differentially expressed genes in synovial fibroblasts by restriction fragment differential display", Rheumatology, 43(11):1346-1352 (Aug. 2004).
Schall, "Biology of the Rantes/sis Cytokine Family", Cytokine, 3(3):165-183 (May 1991).
Schall, et al., "Chemokines, leukocyte trafficking, and inflammation", Curr. Opin, Immunol., 6:865-873 (1994).
Science IP Search Results (Dec. 16, 2004).
Science IP Search Results (Mar. 29, 2006).
Scifinder Search Results (Jan. 24, 2006)—ether linker.
Scifinder Search Results (Jan. 24, 2006)—keto linker.
Segerer, et al., "Chemokines, Chemokine Receptors, and Renal Disease: From Basic Science to Pathophysiologic and Therapeutic Studies", J. Am. Soc. Nephrol., 11:152-176 (2000).
Sell, et al. "Monocyte Chemotactic Protein-1 Is a Potential Player in the Negative Cross-Talk between Adipose Tissue and Skeletal Muscle", Endocrinology, pp. 2458-2467 (2006).
Shadidi, et al., "The Chemokines CCL5, CCL2 and CXCL12 Play Significant Roles in the Migration of Th1 Cells into Rheumatoid Synovial Tissue", Scandinavia Journal of Immunology, 57:192-198 (2003).
Shimizu, et al., "Anti-Monocyte Chemoattractant Protein-1 Gene Therapy Attenuates Renal Injury Inducted by Protein-Overload Proteinuria", J. Am. Soc. Nephrol., 14:1496-1505 (2003).
Sprecher, et al, "Methylated purines and pyrimidines, II Synthesis and properties 2,6-diamino-5-(methylamino)-4-pyrimidinol," Biochemistry, 4(4):655-661 (1965).
Stephan, et al., "Urinary Concentration and Tissue Messenger RNA Expression of Monocyte Chemoattractant Protein-1 As an Indicator of the Degree of Hydronephrotic Atrophy in Partial Ureteral Obstruction", The Journal of Urology, 167:1497-1502 (Mar. 2002).
Takahashi, et al., "Adiposity Elevates Plasma MCP-1 Levels Leading to the Increased CD11b-positive Monocytes in Mice", The Journal of Biological Chemistry, 278(47):46654-46660 (Nov. 2003).
Targan, et al., "A Short-Term Study of Chimeric Monoclonal Antibody cA2 to Tumor Necrosis Factor .alpha. For Crohn's Disease", N. Engl. J. Med., 337(15):1029-1035 (1997).
Taylor, et al., "Reduction of Chemokine Levels and Leukocyte Traffic to Joints by Tumor Necrosis Factor .alpha. Blockade in Patients with Rheumatoid Arthritis," Arthritis & Rheumatism, 43(1):38-47 (Jan. 2000).
Tedder et al., "Structure-based design, synthesis, and antimicrobial activity of purine derived SAH/MTA nucleosidase Inhibitors", Bioorganic & Medicinal Chemistry Letters, 14:3165-3168 (2004).
Trentham, et al., "Autoimmunity to Type II Collagen: An Experimental Model of Arthritis," J. Exp. Med., 146:857-868 (1977).
Tucci, et al., "Synovial Tissues Collected from Rheumatoid Patients Undergoing Total Joint Arthroplasty Express Markers for Acute Inflammation", Biomedical Sciences Instrumentation, 34:169-174 (1997).
Uehara, et al., "A Role for CCR9 in T Lymphocyte Development and Migration", J. Immunol., 168(6):2811-2819 (2002).
Ueno, et al., "Significance of Macrophage Chemoattractant Protein-1 in Macrophage Recruitment, Angiogenesis, and Survival in Human Breast Cancer", Clinical Cancer Research, 6:3282-3289 (Aug. 2000).
Vande Broek, et al., "Chemokine receptor CCR2 is expressed by human multiple myeloma cells and mediates migration to bone marrow stromal cell-produced monocyte chemotactic proteins MCP-1, -2 and -3", British Journal of Cancer, 88:855-862 (2003).
VanRiper, et al., "Characterization and Species Distribution of High Affinity GTP-coupled Receptors for Human Rantes and Monocyte Chemoattractant Protein 1", J. Exp. Med., 177:851-856 (Mar. 1993).
Vervoordeldonk, et al., "Cytokines in Rheumatoid Arthritis", Current Rheumatology Reports, 4:208-217 (2002).
Vestergaard, et al., "Expression of CCR2 on Monocytes and Macrophages in Chronically Inflamed Skin in Atopic Dermatitis and Psoriasis", Acta. Derm. Venereol., 84(5):353-358 (2004).
Villiger, et al., "Production of Monocyte Chemoattractant Protein-1 by Inflamed Synovial Tissue and Cultured Synoviocytes", J Immunol., 149(2):722-727 (1992).
Weisberg, et al., "CCR2 modulates inflammatory and metabolic effects of high-fat feeding", The Journal of Clinical Investigation, 116(1):115-124 (Jan. 2006).
Weisberg, et al., "Obesity is associated with macrophage accumulation in adipose tissue", J Clin. Invest., 112 (12):1796-1808 (2003).
Wurbel, et al., "Mice lacking the CCR9 CC-chemokine receptor show a mile impairment of early T-and B-cell development and a reduction in T-cell receptor y +", Blood, 98(9):2626-2632 (2001).
Xu, et al., "Chronic inflammation in fat plays a crucial role in the development of obesity-related insulin resistance", J Clin. Invest., 112(12):1821-1830 (2003).
Yang, et al., "Phenotypic Charact6eristics of infiltrated inflammatory cells, renal tubular epithelial cells and interstitial cells and their possible roles in the outcome of human drug-associated interstitial nephritis", National Medical Journal of China, 81(2):73-77 (Jan. 2001).
Yogi, Seiichi, et al., "Synthesis of imido-substituted 3,8-diphenyl-1,2-diazacycloocta-2,4,6,8-tetraenes and their thermolysis," Bull. Chem. Soc. Jpn., 60:731-735 (1987).
Yoshimatsu, K., et al. "Mechanism of action of E7010, an orally active sulfonamide antitumor agent: Inhibition of mitosis by binding to the clochicine site of tubulin," Cancer Research, 57(15):3208-3218 (1997).
Yoshino, et al., "Novel Sulfonamides as Potential, Systemically Active Antitumor Agents", J. Med. Chem., 35:2496-2497 (1992).
Youn, et al., "Role of the CC Chemokine receptor 9/TECK interaction in apoptosis", Apoptosis, 7(3):271-276 (2002).
Zaballos, et al., "Cutting Edge: Identification of the Orphan Chemokine Receptor CPR-9-6 as CCR9, the Receptor for the Chemokine TECK," J. Immunol., 162:5671-5675 (1999).
McDonald, Francis G., et al., "Pyrazine Chemistry. II. Derivatives of 3-Hydroxypyrazinoic Acid," J. Am. Chem. Soc., 69(5):1034-1037 (1947).
Tsuge, O., et al., "Synthesis of Imido-Substituted 3,8-Diphenyl-1,2-diazacycloocta-2,4,6,8-tetraenes and Their Thermolysis," Bull Chem. Soc. Jpn. 60:731-735 (1987).
National Kidney Foundation, "Focal Segmental Glomerulosclerosis (FSGS)," https://www.kidney.org/atoz/content/focal (accessed Mar. 29, 2019) (Year: 2019).
Sayyed et al., "An Orally Active Chemokine Receptor CCR2 Antagonist Prevents Glomerulosclerosis and Renal Failure in Type 2 Diabetes," Kidney Int, vol. 80, (2011), pp. 68-78.
Kim et al., "Secondary Focal Segmental Glomerulosclerosis from Podocyte Injury to Glomerulosclerosis," BioMed Research International, (2016).

(56) References Cited

OTHER PUBLICATIONS

CCX140-PubChem Open Chemistry Database, accessed Nov. 15, 2018.
Roberts, "Dimerix's Phase 2 Success for DMS-200—An Important Potential New Treatment Option for Kidney Disease," Livewire, published Jul. 13, 2017.
Kiffel et al., "Focal Segmental Glomerulosclerosis and Chronic Kidney Disease in Pediatric Patients," Adv. Chronic Kidney Dis., vol. 18, No. 5, (2011), pp. 332-338.
Ayoub et al., "Functional Interaction Between Angiotensin II Receptor Type 1 and Chemokine (C-C Motif) Receptor 2 with Implications for Chronic Kidney Disease," PLOS One, vol. 10, No. 3, (2015), e0119803.
International Search Report and Written Opinion for International Application No. PCT/US2017/063120, dated Mar. 8 2018.
Amann, et al., "ACE Inhibitors Improve Diabetic Nephropathy Through Suppression of Renal MCP-1", Diabetes Care, 26(8)2421-2425 (Aug. 2003).
Babu, et al., "Chemokine Receptors of T Cells and of B Cells in Lymphatic Filarial Infection: A Role for CCR9 in Pathogenesis," Journal of Infectious Diseases, 191:1018-1026 (2005).
Baker, B.R., et al., "Puromycin. Synthetic studies. II. The position of glycosidation on the 6-dimethylaminopurine moiety," J. Org. Chem., 19:638-645 (1954).
Beilstein Data XP002464251 BRN:7928945 (2000).
Beilstein Data XP002464252 BRN:7313089 (1995).
Beilstein Data XP002464253 BRN:329227 (1949).
Beilstein Data XP002464254 BRN:7102156 (1987).
Beilstein Data XP002464255 BRN:6875780 (1983).
Bendele, et al., "Animal Models of Arthritis: Relevance to Human Disease," Toxicologic Pathology, 27(1):134-142 (1999).
Bendele, et al., "Efficacy of Sustained Blood Levels of Interleukin-1 Receptor Antagonist in Animal Models of Arthritis," Arthritis & Rheum., 42(3):498-506 (1999).
Berge, Stephen M., et al., "Pharmaceutical Salts," J. Pharm. Sci., 66(1):1-19 (Jan. 1977).
Berman, et al.,"Lymphocyte Motility and Lymphocyte Chemoattractant Factors", Immunol. Invest., 17:625-677, 1988.
Bredereck, Hellmutt, et al., "Synthesen in der Purinreihe. XVI. Uber die Darstellung von 5-Alkyl-bzw.5-Arylsulfonylamino-4-amino-uracilen, 4-Amino-5-alkylamino-uracilen und 4-Amino-5- [pyridinio-methylenamino]-uracil-chloriden," Chemische Berichte, 95:1902-1909 (1962).
Broek, I. Vande, et al., "Chemokine receptor CCR2 is expressed by human multiple myeloma cells and mediates migration to bone marrow stromal cell-produced monocyte chemotactic proteins MCP-1, -2 and -3," Br. J. Cancer, 88 (6):855-862 (2003).
Campbell, et al., "Rapid Acquisition of Tissue-specific Homing Phenotypes by CD4+T Cells Activated in Cutaneous or Mucosal Lymphoid Tissues", J. Exp. Med., 195(1):135-141 (2002).
Charo, I., et al., CCX872-B: Pharmacodynamic Study of a Potent and Selective CCR2 Antagonist in Human Volunteers and Clinical Trial Design in Patients with Pancreatic Cancer, ChemoCentryx Poster CT223, 1 page (Apr. 2015).
ChemoCentryx, "ChemoCentryx Announces Immuno-Oncology Data Presentations at the AACR-NCI-EORTC Molecular Targets and Cancer Therapeutics Meeting,"3 pages (Nov. 4, 2015).
ChemoCentryx, "ChemoCentryx Initiates Clinical Trial of CCX872, Its Next-Generation, Orally Administered CCR2 Inhibitor, in Pancreatic Cancer," 3 pages (Apr. 20, 2015).
ChemoCentryx, "ChemoCentryx Reports First Quarter 2015 Financial Results and Provides Corporate Update," 5 pages (May 6, 2015).
ChemoCentryx, "ChemoCentryx Reports Fourth Quarter 2014 Financial Results and Provides Corporate Update," 5 pages (Mar. 12, 2015).
ChemoCentryx, "ChemoCentryx Reports Second Quarter 2015 Financial Results and Provides Corporate Update," 5 pages (Aug. 6, 2015).
ChemoCentryx, "ChemoCentryx Reports Third Quarter 2014 Financial Results and Provides Corporate Update," 5 pages (Nov. 5, 2014).
ChemoCentryx, "ChemoCentryx Reports Third Quarter 2015 Financial Results and Provides Corporate Update," 5 pages (Nov. 9, 2015).
ChemoCentryx, "ChemoCentryx to Hold First Quarter 2015 Financial Results Conference Call on Wednesday, May 6, 2015," 2 pages (Apr. 22, 2015).
ChemoCentryx, "ChemoCentryx to Hold Second Quarter 2015 Financial Results Conference Call on Thursday, Aug. 6, 2015," 2 pages (Jul. 29, 2015).
ChemoCentryx, "ChemoCentryx to Hold Third Quarter 2015 Financial Results Conference Call on Monday, Nov. 9, 2015," 2 pages (Oct. 29, 2015).
ChemoCentryx, "ChemoCentryx to Present at the Rodman & Renshaw 17th Annual Global Investment Conference," 2 pages (Sep. 2, 2015).
ChemoCentryx, "ChemoCentryx to Present at Two Upcoming Investor Conferences," 2 pages (May 12, 2015).
ChemoCentryx, "ChemoCentryx to Present at Two Upcoming Investor Conferences," 2 pages (Nov. 12, 2015).
Christiansen, et al., "Monocyte chemoattractant protein-1 is produced in isolated adipocytes, associated with adiposity and reduced after weight loss in morbid obese subjects", International Journal of Obesity, 29:146-150 (2005).
Dahinden, et al., "Monocyte Chemotactic Protein 3 Is a Most Effective Basophil- and Eosinophil-activating Chemokine", J. Exp. Med., 179:751-756 (1994).
Dai, et al., "Monocyte chemoattractant protein-1 expression in renal tissue is associated with monocyte recruitment and tubule-interstitial lesions in patients with lupus nephritis", Chinese Medical Journal, 114(8):864-868 (2001).
Davidson, et al., "T Helper Cell 1-type CD4+T Cells, but Not B Cells, Mediate Colitis in Interleukin 10-deficient Mice", J. Exp. Med., 184:241-251 (1996).
de Mik, SM, et al., "Pathophysiology and treatment of focal segmental glomerulosclerosis: the role of animal models," BMC Nephrol. 14:74 (Apr. 1, 2013).
Deleuran, et al, "Localization of monocyte chemotactic and activating factor (MCAF/MCP-1) in psoriasis", Journal of Dermatological Science, 13:228-236 (1996).
Diamond, et al., "Macrophages, monocyte chemoattractant peptide-1, and TGF-.beta.1 in experimental hydronephrosis", American Journal of Physiology, 226(6):F926-F933 (Jun. 1994).
Dorwald, "Side Reactions in Organic Synthesis: A Guide to Successful Synthesis Design" Wiley-VCH Verlag GmbH & KGaA, Weinheim, Preface (2005).
Eddy, et al. "Renal expression of genes that promote interstitial inflammation and fibrosis in rats with protein-overload proteinuria", Kidney International, 47:1546-1557 (1995).
Ellingson, et al. "Pyrazine chemistry. III. Derivatives of 3-amino-5,6-dimethylpyrazineic acid," J. Am. Chem. Soc., 70:1257-1261 (1948).
El-Subbagh, et al., "Novel diarylsulphide derivatives as potential cytotoxic agents", Bollettino Chimico Farmaceutico, 134:80-84 (1995).
Eskens, Ferry, et al., "Pharmacokinetic and Pharmacodynamic Profile of the Novel, Oral and Selective CCR2 Inhibitor CCX872-B in a Phase 1B Pancreatic Cancer Trial," ChemoCentryx Poster IBCD15-020, 1 page, (Dec. 2015).
Feria, Manuel, et al., "The CCR2 receptor as a therapeutic target," Expert Opinion on Therapeutic Patents, Informa Healthcare, GB, 16(1):49-57 (2006).
Gillitzer, et al., "MCP-1 mRNA Expression in Basal Keratinocytes of Psoriatic Lesions", J. Invest Dermatol, 101:127-131 (1993).
Gong, et al., "An Antagonist of Monocyte Chemoattractant Protein 1 (MCP-1) Inhibits Arthritis in the MRL—Ipr Mouse Model", J. Exp. Med., 186(1):131-137 (Jul. 1997).
Gonzales-Cuadrado, et al., "Expression of leucocyte chemoattractants by interstitial renal fibroblasts: up-regulation by drugs associated with interstitial fibrosis", Clin. Exp. Immunol., 106:518-522 (1996).

(56) References Cited

OTHER PUBLICATIONS

Hezel, Aram, et al., "Pharmacokinetic and Pharmacodynamic Profile of a Novel Orally-administered CCR2 Inhibitor, CCX872-B, in a Pancreatic Cancer Trial," ChemoCentryx Poster B24, 1 page (Nov. 2015).
International Search Report and Written Opinion for International Application No. PCT/US2017/035628 (dated Aug. 29, 2017).
International Search Report and Written Opinion for International Application No. PCT/US2017/037264 (dated Oct. 6, 2017).
International Search Report for International Application No. PCT/US2007/015893 (dated Jan. 22, 2008).
International Search Report for International Application No. PCT/US2007/015785 (dated Oct. 23, 2008).

Vehicle

Compound 1

RAAS Blocker

Compound 1+RAAS Blocker

TREATMENT OF FOCAL SEGMENTAL GLOMERULOSCLEROSIS WITH CCR2 ANTAGONISTS

CROSS-REFERENCES TO RELATED APPLICATIONS

This application is an application claiming benefit under 35 U.S.C. § 119(e) of U.S. Provisional Application No. 62/570,778 filed Oct. 11, 2017, which is incorporated herein by reference in its entirety.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Focal segmental glomerulosclerosis (FSGS) comprises a group of uncommon disorders that present with marked proteinuria, nephrotic syndrome, progressive renal failure and characteristic glomerular lesions on histopathology. The current standard of care for patients with FSGS include immunosuppressive drugs such as glucocorticoids followed by calcineurin inhibitors, if needed, for intolerance or inadequate response to glucocorticoids. Renin-angiotensin-aldosterone (RAAS) blockers are also used to control proteinuria, an important signature of FSGS. Existing treatments, however, achieved only limited success. Despite best care, treatment failure is common and FSGS is causal in a significant proportion of end stage renal disease. Thus, an unmet need exists for novel disease modifying treatments for FSGS.

BRIEF SUMMARY OF THE INVENTION

Provided herein are methods of treating focal segmental glomerulosclerosis, said methods comprising administering to a subject in need thereof a therapeutically effective amount of a CCR2 antagonist.

In some embodiments, the CCR2 antagonist is a compound of Formula I

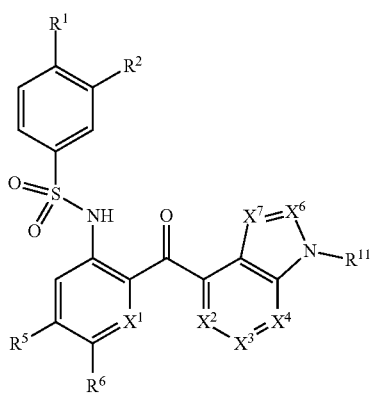

(I)

or a pharmaceutically acceptable form thereof, wherein
$R^1$ and $R^2$ are each independently selected from the group consisting of hydrogen, halogen, $C_{1-8}$ alkyl, CN, or $C_{1-8}$ haloalkyl, provided that at least one of $R^1$ or $R^2$ is other than hydrogen;
$R^5$ is halogen or $C_{1-8}$ alkyl;
$R^6$ is hydrogen or $C_{1-8}$ alkyl;
$X^1$ and $X^2$ are each independently is $CR^7$, N, or NO;
$X^4$ is N or NO;
$X^3$ is $CR^7$;
$X^6$ and $X^7$ are each independently selected from $CR^7$, N, and NO;
$R^7$ is independently selected from the group consisting of hydrogen, halogen, $C_{1-8}$ alkyl, $C_{2-8}$ alkenyl, $C_{2-8}$ alkynyl, —CN, —$NO_2$, —$OC(O)R^8$, —$CO_2R^8$, —$C(O)R^8$, —$C(O)NR^9R^8$, —$OC(O)NR^9R^8$, —$NR^{10}C(O)R^8$, —$NR^{10}C(O)NR^9R^8$, —$NR^9R^8$, —$NR^{10}CO_2R^8$, —$SR^8$, —$S(O)R^8$, —$S(O)_2R^8$, —$S(O)_2NR^9R^8$, —$NR^{10}S(O)_2R^8$, $C_{6-10}$ aryl, 5- to 10-membered heteroaryl and 3- to 10-membered heterocyclyl;
each $R^8$, $R^9$ and $R^{10}$ is independently selected from the group consisting of hydrogen, $C_{1-8}$ alkyl, $C_{2-8}$ alkenyl, $C_{2-8}$ alkynyl, aryl, or heteroaryl; or $R^9$ and $R^8$ or $R^{10}$ and $R^8$, together with the atom(s) to which they are attached, form a 5-, 6-, or 7-membered ring;
$R^{11}$ is selected from the group consisting of hydrogen, $C_{1-8}$ alkyl, $C_{2-8}$ alkenyl, $C_{2-8}$ alkynyl, $C_{6-10}$ aryl, 5- to 10-membered heteroaryl and 3- to 10-membered heterocycle.

In some embodiments, the CCR2 antagonist is a compound of Formula II

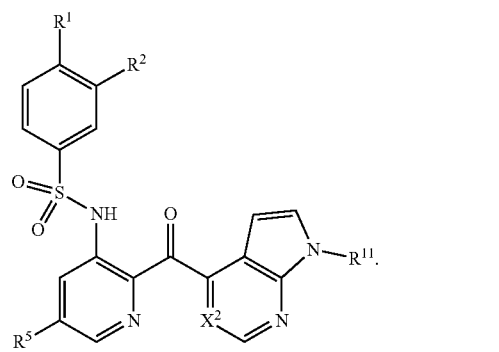

(II)

In some embodiments, the CCR2 antagonists are administered in combination with an additional therapeutic agent.

DETAILED DESCRIPTION OF THE INVENTION

I. General

Figure 1:
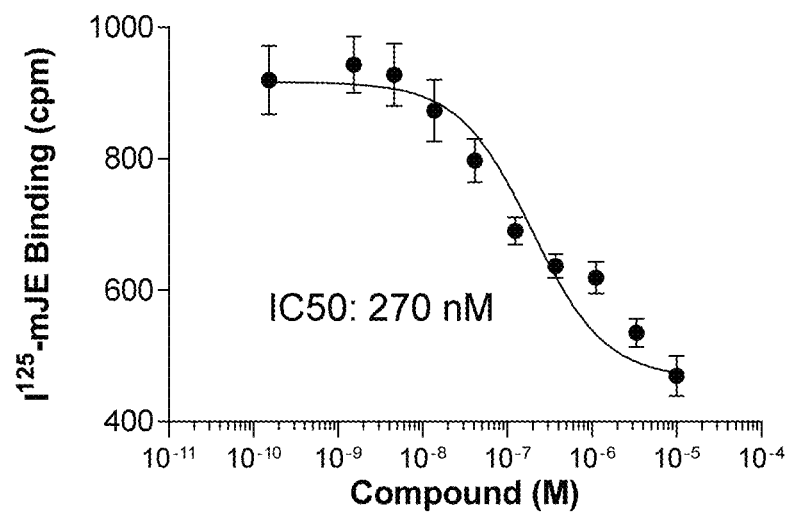
FIG. 1 illustrates the titration of Compound 1 and the inhibition of radio-labeled mJE binding to WEHI cells. Compound 1 was added at the indicated concentrations and competed with the binding of murine CCL2 (JE) to the cells, as described in Methods. The $IC_{50}$ was determined to be 270 nM.

Provided herein are methods of treating focal segmental glomerulosclerosis using a CCR2 antagonist. CCR2 antagonists may be administered as a monotherapy or in combination. In some embodiments, CCR2 antagonists are administered as a monotherapy. In some embodiments, CCR2 antagonists are administered in combination with a Renin-angiotensin-aldosterone (RAAS) blocker. In some embodiments, CCR2 antagonsits are administered in combination with an endothelin receptor antagonist. In some embodiments, CCR2 antagonists are administered in combination with a Renin-angiotensin-aldosterone (RAAS) blocker and an endothelin receptor antagonist.

II. Definitions

As used herein the term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., $C_{3-6}$cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2] octane, etc. The term "heterocycloalkane", "heterocycloalkyl", or "heterocyclyl" refers to a cycloalkyl group that contain from one to five heteroatoms selected from N, O, and S, wherein the nitrogen and sulfur atoms are optionally oxidized, and the nitrogen atom(s) are optionally quaternized. The heterocycloalkane may be a monocyclic, a bicyclic or a polycyclic ring system. Non limiting examples of heterocycloalkane groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrhydrothiophene, quinuclidine, and the like. A heterocycloalkane group can be attached to the remainder of the molecule through a ring carbon or a heteroatom.

As used herein, the term "alkylene" by itself or as part of another substituent means a divalent radical derived from an alkane, as exemplified by —CH$_2$CH$_2$CH$_2$CH$_2$—. Typically, an alkyl (or alkylene) group will have from 1 to 24 carbon atoms, with those groups having 10 or fewer carbon atoms being preferred in the present disclosure. A "lower alkyl" or "lower alkylene" is a shorter chain alkyl or alkylene group, generally having four or fewer carbon atoms. Similarly, "alkenylene" and "alkynylene" refer to the unsaturated forms of "alkylene" having double or triple bonds, respectively. The term "heteroalkylene" refers to an alkylene group in which one or two carbon atoms are replaced by N, O, or S.

As used herein, a wavy line, "⌇", that intersects a single, double or triple bond in any chemical structure depicted herein, represent the point attachment of the single, double, or triple bond to the remainder of the molecule.

As used herein, the terms "halo" or "halogen," by themselves or as part of another substituent, mean, unless otherwise stated, a fluorine, chlorine, bromine, or iodine atom. Additionally, terms such as "haloalkyl" and "haloalkoxy," are meant to include monohalo- and polyhalo-versions of alkyl and alkoxy, respectively. For example, the term "$C_{1-4}$ haloalkyl" is mean to include trifluoromethyl, 2,2,2-trifluoroethyl, 4-chlorobutyl, 3-bromopropyl, and the like.

As used herein, the term "aryl" or "aromatic ring" means, unless otherwise stated, a polyunsaturated, typically aromatic, hydrocarbon group which can be a single ring or multiple rings (up to three rings) which are fused together or linked covalently. Similarly, the terms "heteroaryl" and "heteroaromatic ring" refer to aryl groups (or rings) that contain from one to five heteroatoms selected from N, O, and S, wherein the nitrogen and sulfur atoms are optionally oxidized, and the nitrogen atom(s) are optionally quaternized. A heteroaryl group or heteroaromatic ring can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for each of the above noted aryl and heteroaryl ring systems are selected from the group of acceptable substituents described below.

As used herein, the term "heteroatom" is meant to include oxygen (O), nitrogen (N), sulfur (S) and silicon (Si).

As used herein the term "oxo" refers to a double bonded oxygen (=O).

As used herein, the term "pharmaceutically acceptable salts" is meant to include salts of the active compounds which are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

In addition to salt forms, the present disclosure provides compounds which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

Certain compounds of the present disclosure can exist in unsolvated forms as well as solvated forms, including hydrated forms. In general, the solvated forms are equivalent to unsolvated forms and are intended to be encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

Certain compounds of the present disclosure possess asymmetric carbon atoms (optical centers) or double bonds; the racemates, diastereomers, geometric isomers, regioisomers and individual isomers (e.g., separate enantiomers) are all intended to be encompassed within the scope of the present disclosure. When a stereochemical depiction is shown, it is meant to refer the compound in which one of the isomers is present and substantially free of the other isomer. 'Substantially free of' another isomer indicates at least an 80/20 ratio of the two isomers, more preferably 90/10, or 95/5 or more. In some embodiments, one of the isomers will be present in an amount of at least 99%.

The compounds of the present disclosure may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3H$), iodine-125 ($^{125}I$) or carbon-14 ($^{14}C$), or non-radioactive isotopes, such as deuterium ($^2H$) or carbon-13 ($^{13}C$). Such isotopic variations can provide additional utilities to those described elsewhere with this application. For instance, isotopic variants of the compounds of the disclosure may find additional utility, including but not limited to, as diagnostic and/or imaging reagents, or as cytotoxic/radiotoxic therapeutic agents. Additionally, isotopic variants of the compounds of the disclosure can have altered pharmacokinetic and pharmacodynamic characteristics which can contribute to enhanced safety, tolerability or efficacy during treatment. All isotopic variations of the compounds of the present disclosure, whether radioactive or not, are intended to be encompassed within the scope of the present disclosure. Substitution with heavier isotopes such as deuterium, i.e. $^2$H, may afford certain therapeutic advantages resulting from greater metabolic stability. For example, in vivo half-life may increase or dosage requirements may be reduced.

As used herein, the terms "subject", "patient" or "individual" are used herein interchangeably to include a human or animal. For example, the animal subject may be a mammal, a primate (e.g., a monkey), a livestock animal (e.g., a horse, a cow, a sheep, a pig, or a goat), a companion animal (e.g., a dog, a cat), a laboratory test animal (e.g., a mouse, a rat, a guinea pig, a bird), an animal of veterinary significance, or an animal of economic significance.

As used herein, the term "urine albumin-to-creatinine ratio" refers to the ratio of albumin to creatinine as measured in a subject's urine sample (e.g. (urine albumin/urine creatinine). This is a common measure used to determine kidney function, because when the kidneys are functioning properly, little to no albumin is found in the urine and creative is normally released into the urine at a relatively constant rate.

As used herein, the term "therapeutically effective amount" means the amount of the subject compound that will elicit the biological or medical response of a cell, tissue, system, or animal, such as a human, that is being sought by the researcher, veterinarian, medical doctor or other treatment provider.

As used herein, the term "selective CCR2 antagonist" refers to a highly discriminatory compound that inhibits normal CCR2 activity with little or no cross reactivity on non-targeted proteins such as CCR1, CCR3, CCR4, CCR5, CCR6, CCR7, CCR8, CCR9, CCR10, FPRL2, CXCR1, CXCR2, CXCR3, CXCR4, CXCR5, CXCR6, CXCR7, C3aR, and/or C5aR. In some embodiments, "selective CCR2 antagonists" have an $IC_{50}$ that is at least 10, 100, 500, 1,000, 5,000, 10,000 or more times lower than for that of proteins such as CCR1, CCR3, CCR4, CCR5, CCR6, CCR7, CCR8, CCR9, CCR10, FPRL2, CXCR1, CXCR2, CXCR3, CXCR4, CXCR5, CXCR6, CXCR7, C3aR, and/or C5aR when measured in the assay types described in Example 3 of this application. In some embodiments, "selective CCR2 antagonists" do not inhibit the activity of CCR1, CCR3, CCR4, CCR5, CCR6, CCR7, CCR8, CCR9, CCR10, FPRL2, CXCR1, CXCR2, CXCR3, CXCR4, CXCR5, CXCR6, CXCR7, C3aR, and/or C5aR at concentrations of 1 μM or below in assay types described in Example 3 of this application. The above-mentioned proteins are considered to be "not inhibited" when they maintain 100%, 99%, 95%, 90%, or 85% of their activity under the referenced conditions with a selective CCR2 antagonist.

As used herein, the term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

III. Methods of Treating Focal Segmental Glomerulosclerosis

Provided method of treating focal segmental glomerulosclerosis, said method comprising administering to a subject in need thereof a therapeutically effective amount of a CCR2 antagonist.

In some embodiments, the CCR2 antagonist is a compound of Formula I

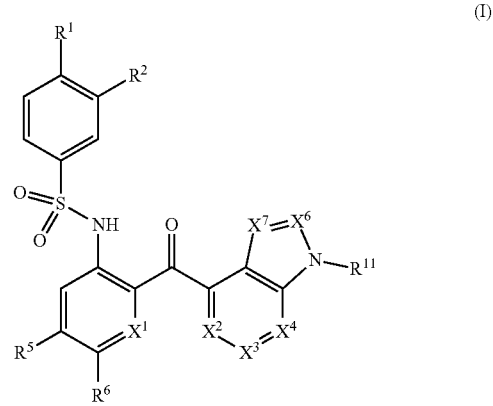

or a pharmaceutically acceptable form thereof, wherein $R^1$ and $R^2$ are each independently selected from the group consisting of hydrogen, halogen, $C_{1-8}$ alkyl, CN, or $C_{1-8}$ haloalkyl, provided that at least one of $R^1$ or $R^2$ is other than hydrogen;

$R^5$ is halogen or $C_{1-8}$ alkyl;

$R^6$ is hydrogen or $C_{1-8}$ alkyl;

$X^1$ and $X^2$ are each independently is $CR^7$, N, or NO;

$X^4$ is N or NO;

$X^3$ is $CR^7$;

$X^6$ and $X^7$ are each independently selected from $CR^7$, N, and NO;

$R^7$ is independently selected from the group consisting of hydrogen, halogen, $C_{1-8}$ alkyl, $C_{2-8}$ alkenyl, $C_{2-8}$ alkynyl, —CN, —NO$_2$, —OC(O)R$^8$, —CO$_2$R$^8$, —C(O)R$^8$, —C(O)NR$^9$R$^8$, —OC(O)NR$^9$R$^8$, —NR$^{10}$C(O)R$^8$, —NR$^{10}$C(O)NR$^9$R$^8$, —NR$^9$R$^8$, —NR$^{10}$CO$_2$R$^8$, —SR$^8$, —S(O)R$^8$, —S(O)$_2$R$^8$, —S(O)$_2$NR$^9$R$^8$, —NR$^{10}$S(O)$_2$R$^8$, $C_{6-10}$ aryl, 5- to 10-membered heteroaryl and 3- to 10-membered heterocyclyl;

each $R^8$, $R^9$ and $R^{10}$ is independently selected from the group consisting of hydrogen, $C_{1-8}$ alkyl, $C_{2-8}$ alkenyl, $C_{2-8}$ alkynyl, aryl, or heteroaryl; or $R^9$ and $R^8$ or $R^{10}$ and $R^8$, together with the atom(s) to which they are attached, form a 5-, 6-, or 7-membered ring;

$R^{11}$ is selected from the group consisting of hydrogen, $C_{1-8}$ alkyl, $C_{2-8}$ alkenyl, $C_{2-8}$ alkynyl, $C_{6-10}$ aryl, 5- to 10-membered heteroaryl and 3- to 10-membered heterocycle.

In some embodiments, the compound of Formula I has the structure of Formula II (II)

[Chemical structure of Formula II: a benzene ring with R¹ and R² substituents, connected via a sulfonamide (SO₂NH) group to a pyridine ring bearing R⁵, which is connected via a carbonyl (C=O) to a pyrrolo-fused heterocycle with X² and N-R¹¹]

or a pharmaceutically acceptable form thereof.

In some embodiments of the compound of Formula II,
R¹ and R² are each independently selected from the group consisting of halogen, $C_{1-8}$ alkyl, or $C_{1-8}$ haloalkyl, provided that at least one of R¹ or R² is other than hydrogen;
R⁵ is halogen or $C_{1-8}$ alkyl;
X² is CR⁷ or N;
R⁷ is independently selected from the group consisting of hydrogen, halogen, $C_{1-8}$ alkyl, —CN, —NO₂, —OR⁸, and —NR⁹R⁸;
R¹¹ is hydrogen or $C_{1-8}$ alkyl.

In some embodiments of the compound of Formula II,
R¹ is halogen
R² $C_{1-8}$ haloalkyl;
R⁵ is $C_{1-8}$ alkyl;
X² is CR⁷ or N;
R⁷ is independently selected from the group consisting of hydrogen, halogen, $C_{1-8}$ alkyl;
R¹¹ is hydrogen or $C_{1-8}$ alkyl.

In some embodiments of the compound of Formula II,
R¹ is chloro
R² trifluoromethyl;
R⁵ is methyl;
X² is CR⁷ or N;
R⁷ is independently selected from the group consisting of hydrogen, halogen, $C_{1-8}$ alkyl;
R¹¹ is hydrogen or $C_{1-8}$ alkyl.

In some embodiments, the compound of Formula II has the structure of Compound 1

(Compound 1)

[Chemical structure of Compound 1: 4-chloro-3-(trifluoromethyl)benzenesulfonamide linked to a 5-methylpyridine bearing a carbonyl group attached to a 7-azaindole (pyrrolo[2,3-b]pyridine)]

or a pharmaceutically acceptable form thereof.

In some embodiments, the compound of Formula II has the structure of Compound 2

(Compound 2)

[Chemical structure of Compound 2: 4-chloro-3-(trifluoromethyl)benzenesulfonamide linked to a 5-methylpyridine bearing a carbonyl group attached to a 7-deazapurine (pyrrolo[2,3-d]pyrimidine)]

or a pharmaceutically acceptable form thereof.

In some embodiments, the CCR2 antagonist is a selective CCR2 antagonist. Selective CCR2 antagonists are highly discriminatory compounds that have little or no cross reactivity with other chemokine receptors. In some embodiments, selective CCR2 antagonists have an $IC_{50}$ that is at least 10, 100, 500, 1,000, 5,000, 10,000 or more times lower than for that of proteins such as CCR1, CCR3, CCR4, CCR5, CCR6, CCR7, CCR8, CCR9, CCR10, FPRL2, CXCR1, CXCR2, CXCR3, CXCR4, CXCR5, CXCR6, CXCR7, C3aR, and/or C5aR when measured in the assay types described in Example 3 of this application. In some embodiments, selective CCR2 antagonists do not inhibit the activity of CCR1, CCR3, CCR4, CCR5, CCR6, CCR7, CCR8, CCR9, CCR10, FPRL2, CXCR1, CXCR2, CXCR3, CXCR4, CXCR5, CXCR6, CXCR7, C3aR, and/or C5aR at concentrations of 1 μM or below in assay types described in Example 3 of this application. The above-mentioned proteins are considered to be "not inhibited" when they maintain 100%, 99%, 95%, 90%, or 85% of their activity under the referenced conditions with a selective CCR2 antagonist. In some embodiments, the above-mentioned proteins maintain 100% of their activity under the referenced conditions with a selective CCR2 antagonist. In some embodiments, the above-mentioned proteins maintain 99% of their activity under the referenced conditions with a selective CCR2 antagonist. In some embodiments, the above-mentioned proteins maintain 95% of their activity under the referenced conditions with a selective CCR2 antagonist. In some embodiments, the above-mentioned proteins maintain 90% of their activity under the referenced conditions with a selective CCR2 antagonist. In some embodiments, the above-mentioned proteins maintain 85% of their activity under the referenced conditions with a selective CCR2 antagonist.

Individuals with normal kidney function have little or no albumin in the urine. On the other hand, creatinine is normally released into the urine at a constant rate. Thus, the albumin to creatinine ration in a subject's urine can be used as a metric of kidney function. Accordingly, in some embodiments, administration of the CCR2 antagonist to the subject in need thereof reduces a urine albumin-to-creatinine ratio in said subject.

In some embodiments, the urine albumin-to-creatinine ratio in said subject is reduced by at least 20% after 3 weeks of administering the CCR2 antagonist. In some embodiments, the urine albumin-to-creatinine ratio in said subject is reduced by at least 30% after 3 weeks of administering the CCR2 antagonist. In some embodiments, the urine albumin-to-creatinine ratio in said subject is reduced by at least 40% after 3 weeks of administering the CCR2 antagonist. In some embodiments, the urine albumin-to-creatinine ratio in said subject is reduced by at least 50% after 3 weeks of administering the CCR2 antagonist. In some embodiments, the urine albumin-to-creatinine ratio in said subject is reduced by at least 60% after 3 weeks of administering the CCR2 antagonist In the treatment or prevention of focal segmental glomerulosclerosis an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5, 0.5 to 5.0, or 5.0 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day. In some embodiments, the CCR2 antagonist is administered daily.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex, diet, mode and time of administration, rate of excretion, drug combination, the severity of the particular condition, and the host undergoing therapy.

IV. Combination Therapy

In some embodiments, methods of treating focal segmental glomerulosclerosis include administering the CCR2 antagonists described herein as part of combination therapy.

In some embodiments, the additional therapeutic agent is a Renin-angiotensin-aldosterone (RAAS) blocker. In some embodiments, the additional therapeutic agent is an endothelin receptor antagonist. In some embodiments, the additional therapeutic agent is a Renin-angiotensin-aldosterone (RAAS) blocker, and an endothelin receptor antagonist.

RAAS blockers include Renin inhibitors, ACE inhibitors, and angiotensin receptor blockers. As such, in some embodiments, the RAAS blocker is a renin inhibitor. In some embodiments, the RAAS blocker is an ACE inhibitor. In some embodiments, the RAAS blocker is an angiotensin receptor blocker (ARB).

In some embodiments, the renin inhibitor is selected from the group consisting of aliskiren, remikiren, H-142, SPP635, SPP1148, SPP676, SPP1234, or combinations thereof.

In some embodiments, the ACE inhibitor is selected from the group consisting of benazepril (tradename Lotensin®), captopril (tradename Capoten®), enalapril (tradename Vasotec®), fosinopril (tradename Monopril®), lisinopril (tradename Prinivil®, Zestril®), perindopril (tradename Aceon®), quinapril (tradename Accupril®), rampipril (tradename Altace®), trandolapril (tradename (Mavik®), or combinations thereof.

In some embodiments, the angiotensin receptor blocker (ARB) is selected from the group consisting of eprosartan (tradename Teveten®), candesartan (tradename Atacand®), irbesartan (tradename Avapro®), losartan (tradename Cozaar®), olmesartan (tradename Benicar®), telmisartan (tradename Micardis®), valsartan (tradename Diovan®), CGP-42112A, DuP753, saralasin, sarthran, or combinations thereof. In some embodiments, the angiotensin receptor blocker (ARB) is selected from the group consisting of sparsentan, eprosartan (tradename Teveten®), candesartan (tradename Atacand®), irbesartan (tradename Avapro®), losartan (tradename Cozaar®), olmesartan (tradename Benicar®), telmisartan (tradename Micardis®), valsartan (tradename Diovan®), CGP-42112A, DuP753, saralasin, sarthran, or combinations thereof. In some embodiments, the angiotensin receptor blocker (ARB) is sparsentan. A person of skill in the art will recognized that spartsentan is a dual-acting receptor antagonist for endothelin (A type) receptors and angiotensin II receptors.

In some embodiments, the endothelin receptor antagonist is selected from the group consisting of sparsentan, bosentan, macitentan, ambrisentan, sitazentan, aprocitentan, and artasentan. In some embodiments, the endothelin receptor antagonist is selected from the group consisting of bosentan, macitentan, ambrisentan, sitazentan, aprocitentan, and artasentan. In some embodiments, the endothelin receptor antagonist is sparsentan. A person of skill in the art will recognized that spartsentan is a dual-acting receptor antagonist for endothelin (A type) receptors and angiotensin II receptors.

In some embodiments, the amount of additional therapeutic agent is sub-therapeutic when the administered alone. Those of skill in the art will appreciate that "combinations" can involve combinations in treatments (i.e., two or more drugs can be administered as a mixture, or at least concurrently or at least introduced into a subject at different times but such that both are in the bloodstream of a subject at the same time). Additionally, compositions of the current disclosure may be administered prior to or subsequent to a second therapeutic regimen.

The weight ratio of the CCR2 antagonists of the present disclosure to the second active ingredient may be varied and will depend upon the effective dose of each ingredient. Generally, an effective dose of each will be used.

V. Pharmaceutical Compositions

The pharmaceutical compositions for the administration of the compounds of this disclosure may conveniently be presented in unit dosage form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect.

The pharmaceutical compositions containing the active ingredient may be in a form suitable for oral use, for example, as tablets, troches, lozenges, aqueous or oily suspensions, dispersible powders or granules, emulsions and self-emulsifications as described in U.S. Pat. No. 6,451,339, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated enterically or otherwise by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the disclosure may also be in the form of oil in water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. Oral solutions can be prepared in combination with, for example, cyclodextrin, PEG and surfactants.

The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution and isotonic sodium chloride solution. In addition, sterile, axed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present disclosure may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols. Additionally, the compounds can be administered via ocular delivery by means of solutions or ointments. Still further, transdermal delivery of the subject compounds can be accomplished by means of iontophoretic patches and the like.

For topical use, creams, ointments, jellies, solutions or suspensions containing the compounds of the present disclosure are employed. As used herein, topical application is also meant to include the use of mouth washes and gargles.

The pharmaceutical compositions and methods of the present disclosure may further comprise other therapeutically active compounds as noted herein, such as those applied in the treatment of the above mentioned pathological conditions.

In one embodiment, the present disclosure provides a composition consisting of a pharmaceutically acceptable carrier and a compound of the disclosure.

VI. Kits

Also provided herein are kits comprising pharmaceutical compositions of the compound of Formula I or the compound of Formula II, and including kits for combination therapy.

In some aspects, the present invention provides a kit that includes the compound of Formula II or the compound of Formula II. Some of the kits described herein include a label describing a method of administering the compound of Formula I or the compound of Formula II. Some of the kits described herein include a label describing a method of administering the compound of Formula I or the compound of Formula II in combination with one or more (e.g., one, two three, one to two, or one to three) additional therapeutic agents. Some of the kits described herein include a label describing a method of treating focal segmental glomerulosclerosis. In some embodiments, the kits described herein include a label describing a method of reducing urine albumin excretion.

The compositions of the present invention, including but not limited to, compositions comprising Compound 1 and or Compound 2 in a bottle, jar, vial, ampoule, tube, or other container-closure system approved by the United States Food and Drug Administration (FDA) or other regulatory body, which may provide one or more dosages containing the compounds. The package or dispenser may also be accompanied by a notice associated with the container in a form prescribed by a governmental agency regulating the manufacture, use, or sale of pharmaceuticals, the notice indicating approval by the agency. In certain aspects, the kit may include a formulation or composition as described herein, a container closure system including the formulation or a dosage unit form including the formulation, and a notice or instructions describing a method of use as described herein.

EXAMPLES

The following examples are offered for illustrative purposes, and are not intended to limit the invention in any manner. Those of skill in the art will readily recognize a variety of noncritical parameters which can be changed or modified to yield essentially the same results.

Materials & Methods

Cells and Reagents

WEHI-274.1 and ThP1 cells were from ATCC (Rockville, Md.). Human monocytes and neutrophils were isolated from healthy volunteers (Stanford Blood Center, Palo Alto, Calif.) using MACS separation reagents (Miltenyi, Germany). The CCR2 antagonist Compound 1 was discovered and synthesized at ChemoCentryx and stored as a dry powder until the time of formulation for in vivo use. The compound was formulated in 1% hydroxylpropyl methylcellulose (HPMC) (Sigma-Aldrich, St Louis, Mo.) in water for subcutaneous (s.c.) injection at the indicated concentration. Candesartan (AK Scientific, Union City, Calif.) and its vehicle were dosed orally once daily at 5 mg/kg in water. Recombinant chemokines were acquired from R&D Systems (Minneapolis, Minn.). [125I]-CCL2 was from PerkinElmer (Boston, Mass.). Human plasma and mouse plasma were from Bioreclamation (Hicksville, N.Y.)

Mice

Balb/c, 129s and 129X1/SvJ mice were purchased from Jackson Laboratories (Bar Harbor, Me.) and housed at the ChemoCentryx animal facility in accordance with guidelines described in the Guide and Use of Laboratory Animals of the National Research Council. All studies were approved by the ChemoCentryx Institutional Animal Care and Use Committee. All animal studies were conducted under the protocol entitled "Kidney Disease and Diabetes Models in Mice", number CCX176-2008.

Mouse Pharmacokinetic (PK) Study

Compound 1 was formulated in 1% HPMC in water at 6 and 18 mg/mL concentrations, respectively. Five male 129s mice per dose group were injected s.c. with 30 and 90 mg/kg of Compound 1. Blood was drawn at 0.5, 2, 5, 4, 8, 12, and 24 hours post-dosing. Compound 1 drug level was analyzed by LC-MS/MS at ChemoCentryx with plasma samples.

Adriamycin Induced FSGS Model

These experiments were performed using female Balb/c mice (Jackson Laboratories, Bar Harbor, Me.). The mice were kept on standard chow and had free access to water. At age of 10 weeks, 7.5 mg/kg Adriamycin (Selleck Chemicals, Houston, Tex.) or saline (control) was injected via tail vein in isoflurane-anesthetized animals (day 0). Compound 1 and/or vehicle were dosed subcutaneously once daily at 90 mg/kg formulated in 1% HPMC. The RAAS blocker Candesartan (AK Scientific, Union City, Calif.) and its vehicle were dosed orally once daily at 5 mg/kg, formulated in water. All dosing started 2 hours prior Adriamycin challenge. The mice were housed individually in metabolic cages for quantitative collection of urinary albumin and creatinine.

5/6 Nephrectomy Model

5/6 nephrectomy mice on the 129X1/SvJ background were obtained from Jackson Laboratories, and were received at ChemoCentryx after the surgery was performed at JAX. Under isoflurane anesthesia, two-thirds of the left kidney mass was removed at 5-6 weeks of age. Then, after 7 to 10 days, a right unilateral nephrectomy was performed. The mice were fed a standard chow and had free access to water. Three weeks after the 5/6 nephrectomy, the mice were grouped to ensure a similar starting UAER in each treatment group. Compound 1 or its vehicle were dosed subcutaneously once daily formulated in 1% HPMC. The RAAS blocker candesartan (AK Scientific, Union City, Calif.) and its vehicle were dosed orally once daily at 5 mg/kg formulated in water. Sparsentan, the dual-acting receptor antagonist for endothelin (A type) and angiotensin II receptors (Type 1) (Murugesan et al, 2005) was synthesized at ChemoCentryx and was dosed orally twice daily at 90 mg/kg formulated in 1% HPMC. The mice were housed individually in metabolic cages for quantitative collection of urinary albumin and creatinine.

In Vitro Experiments

Chemotaxis, calcium mobilization, and radio-ligand binding assays were conducted as previously described (Sullivan et al, 2013; Walters et al, 2010). Inhibition values ($IC_{50}$) were calculated using non-linear regression with a one-site competition model (GraphPad Prism, GraphPad Software, La Jolla, Calif.). A2 values for assessment of potency in chemotaxis assays denotes the concentration of the antagonist required to right-shift by 2-fold the chemokine dose-response curve. Receptor engagement indices (REIs) were calculated by dividing the plasma concentration of Compound 1 by the measured potency in the chemotaxis assay in 100% mouse serum. Urinary albumin was measured by ELISA (Bethyl Labs, Montgomery, Tex.). Urinary and serum creatinine was measured by LC-MS/MS at Chemo- Centryx. The urinary albumin excretion rate (UAER) was calculated as micrograms per 24 h. Blood urea nitrogen (BUN) was measured by Antech Diagnostics (Morrisville, N.C.). The albumin to creatinine ratio (ACR) was calculated as micrograms of albumin per milligram of creatinine.

Histology

The kidneys were collected, fixed in formalin, embedded in paraffin, and cut into 5-µm-thick sections. Sections were stained with Haematoxylin and Eosin (H&E) (Sigma-Aldrich, St Louis, Mo.) and PAS (Periodic Acid Schiff) (Sigma-Aldrich, St Louis, Mo.) and using standard protocols. Glomerular hypertrophy, mesangial expansion, glomerular sclerosis, and tubular structure were determined by examination of sections by an observer blinded to the treatment groups.

Statistical Methods

Differences between treatment groups were analyzed using Student's t-test.

Example 1: Inhibition of CCL2 Binding in WEHI-274 Murine Monocyte Cell Line Using Compound 1

To determine if CCR2 plays a key role in FSGS we examined the ability of Compound 1 to block radio-labeled CCR2 ligand, mJE (CCL2) binding in the WEHI-274 murine monocyte cell line that endogenously expresses CCR2. As shown in FIG. 1, Compound 1 inhibited mJE binding in WEHI 274 cells with an $IC_{50}$ of 270 nM.

Example 2: Pharmacokinetics of Compound 1 in Mice

Figure 2:
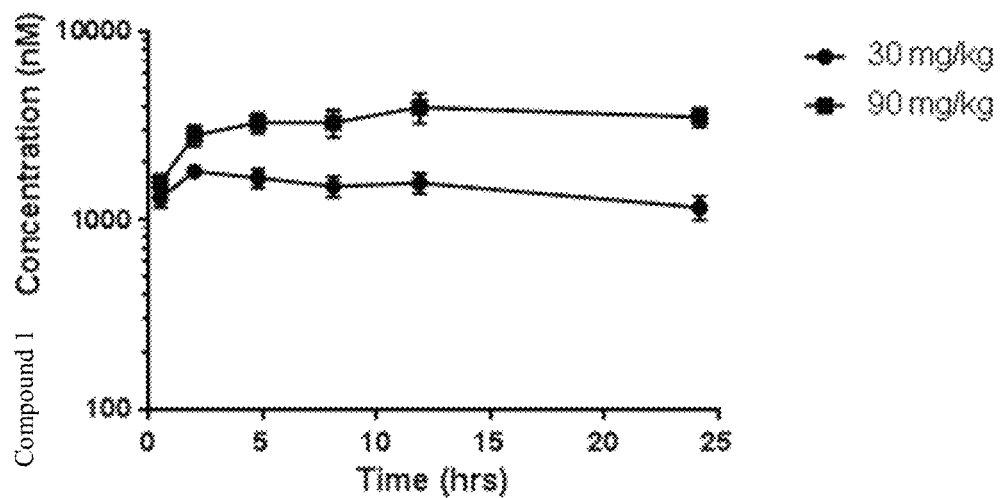
FIG. 2 illustrates the pharmacokinetic profile of Compound 1 in mice. Compound 1 was administered by s.c. injection and the concentration in the blood was determined. Measured levels for 30 mg/kg (black circles) and 90 mg/kg (black squares) are shown.
Figure 3A:
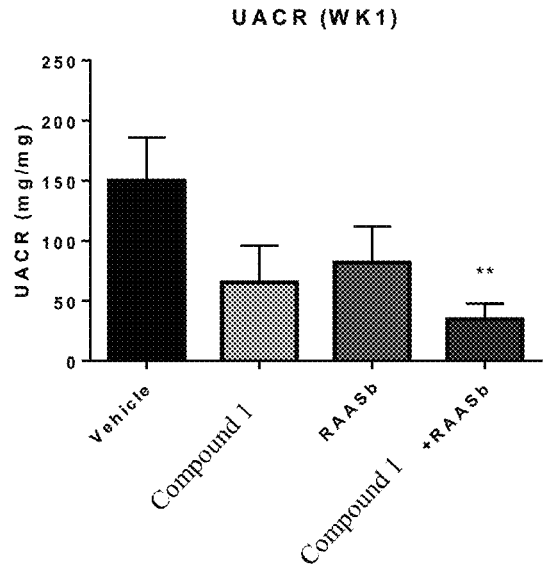
FIG. 3 Compound 1 improves renal function in adriamycin challenged mice. Mice were challenged with Adriamycin as described in Methods. Test compound treatment was begun one hour prior to the Adriamycin challenge. Urine was collected for measurement of albumin and creatinine at the indicated time points (A, week 1; B, week 2), as described in Methods. Serum creatinine (C) and BUN (D) were measured at time of the terminal bleed after two weeks of treatment. Error bars represent standard error of the mean. N=10/group at week 1, and N=8 at week 2.
Figure 3B:
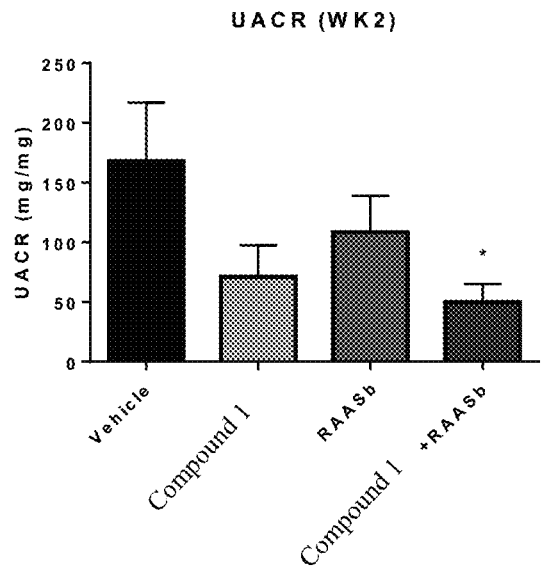
Figure 3C:
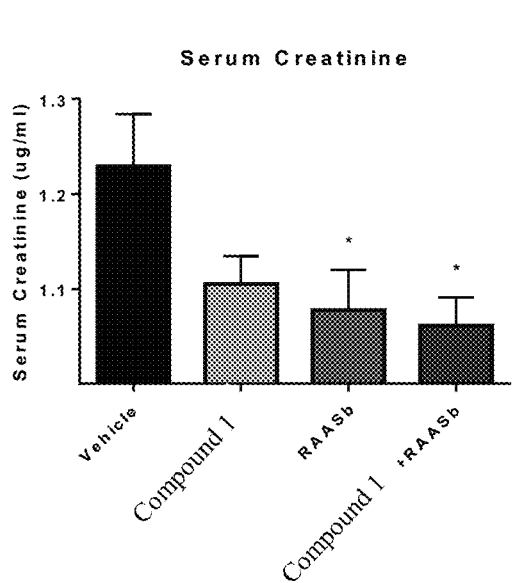
Figure 3D:
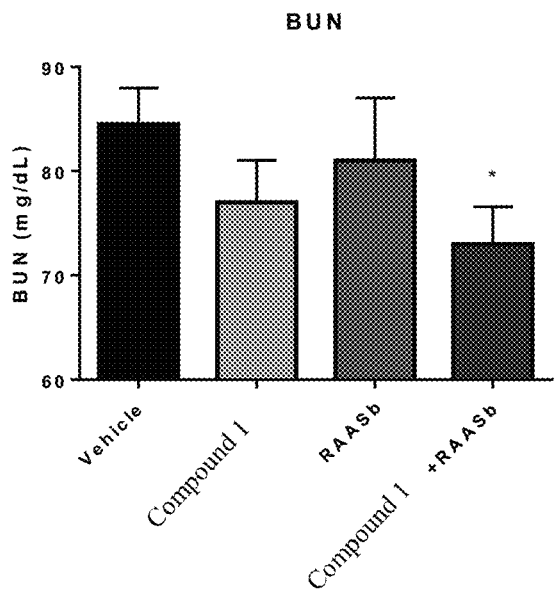

To determine if Compound 1 was suitable for in vivo experiments, we analyzed its pharmacokinetic profile in mice. As shown in FIG. 2, a single s.c. injection of Compound 1 at 90 mg/kg provided a consistent level of Compound 1 in the blood, with a concentration of approximately 3.5 µM, 24 hours post-dosing. We therefore concluded that a once daily s.c. administration of Compound 1 would provide more than adequate CCR2 coverage.

Example 3: Selectivity of Compound 1 Inhibition

To determine the selectivity of Compound 1, we performed a variety of binding-competition and functional assays on cell lines that either endogenously expressed certain chemokine receptors, or were individually transfected with various receptors for other chemokines or chemotactic complement fragments. As summarized in Table 1, Compound 1 did not inhibit any activity in a diverse selection of other receptors even at concentrations well above one micromolar.

TABLE 1

Selectivity Data for Compound 1 on Diverse Family of Human Chemokine and Chemoattractant Receptors

| Receptor | Assay Type | Compound 1 Potency [nM] |
|---|---|---|
| CCR2 | ThP1 Cell Chemotaxis | 0.5 |
| CCR1 | Monocyte Chemotaxis | >10,000 |
| CCR3 | 293-CCR3 Calcium Mobilization | >10,000 |
| CCR4 | Activated Lymphocyte Calcium Mobilization | >10,000 |
| CCR5 | L1.2-CCR5 Chemotaxis | >8,000 |
| CCR6 | Activated Lymphocyte Calcium Mobilization | >8,000 |
| CCR7 | Activated Lymphocyte Calcium Mobilization | >10,000 |
| CCR8 | 293-CCR8 Calcium Mobilization | >10,000 |
| CCR9 | Molt4 Serum Chemotaxis | >10,000 |
| CCR10 | 293-CCR10 Calcium Mobilization | >10,000 |
| FPRL2 | Neutrophil Calcium Mobilization | >10,000 |
| CXCR1 | Neutrophil Calcium Mobilization | >10,000 |
| CXCR2 | Neutrophil Calcium Mobilization | >10,000 |
| CXCR3 | Activated Lymphocyte Calcium Mobilization | >10,000 |
| CXCR4 | Activated Lymphocyte Calcium Mobilization | >10,000 |
| CXCR5 | Baf3-CXCR5 Calcium Mobilization | >10,000 |
| CXCR6 | Activated Lymphocyte Buffer Chemotaxis | >10,000 |
| CXCR7 | 293-CXCR7 Radio-ligand Binding | >10,000 |
| C3aR | Neutrophil Calcium Mobilization | >10,000 |
| C5aR | Neutrophil Calcium Mobilization | >10,000 |

Shown are the $IC_{50}$ values for inhibition of the specified responses.

Example 4: Adriamycin Induced FSGS Model

To evaluate the therapeutic potential of Compound 1 for FSGS, an Adriamycin induced FSGS model was used. Adriamycin is an oncolytic antibiotic that induces proteinuria and glomerulosclerosis in rodents after a single infusion. Rapid reduction in urinary albumin excretion rate (UAER) (mg/day) by Compound 1 alone, or in combination with RAAS blockade in Adriamycin nephropathy model is observed (FIG. 3). Compound 1 as a single agent had achieved a marked reduction in urine albumin-to-creatinine ratio (UACR) by two weeks after the Adriamycin infusion. Adriamycin treated mice displayed significant reduction in UAER in response to Compound 1 alone or in combination with RAAS blockade Table 2). The level of protection was equal to or better than that of RAAS blockade. Combined treatment with Compound 1 and RAAS blocker achieved a statistically significant decrease in UACR with respect to vehicle, accompanied by similar improvements in serum creatinine and BUN levels (FIG. 3).

TABLE 2

Reduction in UAER (mg/day) by Compound 1 alone, or in combination with RAAS blockade in Adriamycin nephropathy model

| | Week 1 | Week 2 |
|---|---|---|
| Vehicle | 75.87 | 89.99 |
| Compound 1 | 26.15, p = 0.06 | 24.19, p = 0.032 |
| RAAS Blocker | 39.46, p = 0.16 | 66.87 |
| Compound 1 + RAAS Blocker | 20.39, p = 0.027 | 23, p = 0.030 |

Example 5: 5/6 Nephrectomy Model

To corroborated the above findings, another FSGS model mechanistically distinct from the Adriamycin approach was tested, the 5/6 nephrectomy model. Beginning three weeks after the completion of surgery, the mice were treated with Compound 1 or RAAS blocker either alone or in combination. As above, renal function was quantified by measuring the UACR, UAER serum creatinine and BUN levels.

Figures 4A, 4B:
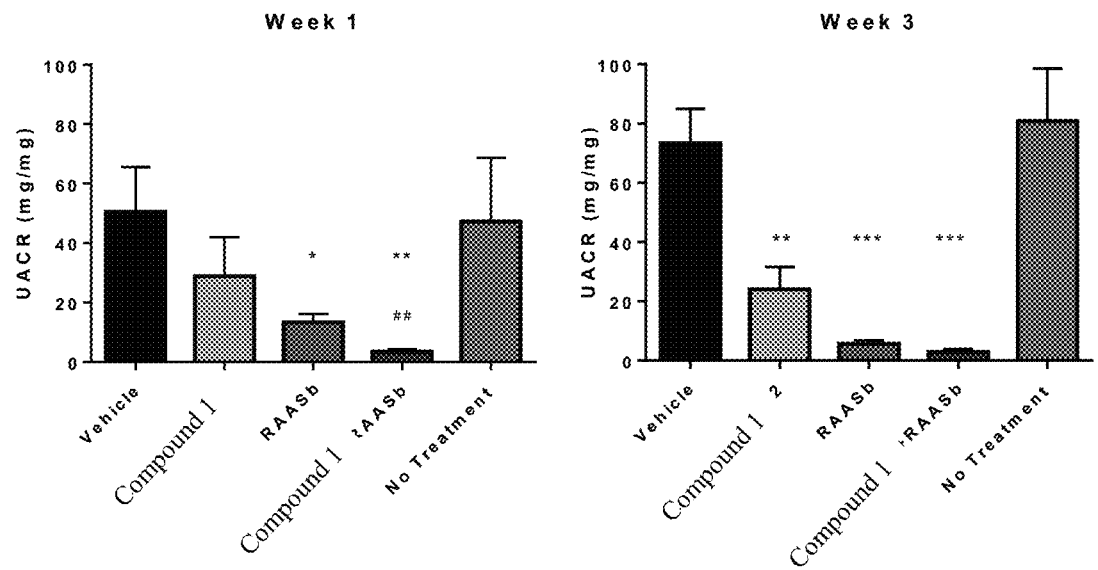
FIG. 4 Compound 1 improves renal function in partially nephrectomized mice. Mice underwent a 5/6 nephrectomy as described in Methods. Three weeks post-surgery the mice were randomized to the groups indicated above for the study period of 4 weeks. Urine was collected for measurement of albumin and creatinine at week 1 (A) and week 3 (B), as described in Methods. Error bars represent standard error of the mean. P<0.05: *; P<0.01: ; P<0.001: *; P value compared to vehicle; P<0.01: ##P value compared to RAASb FIG. 5 Compound 1 attenuates the rise in serum creatinine (A) and BUN (B) in partially nephrectomized mice. Measurements were made at the 4-week time point. Error bars represent standard error of the mean. P<0.05: *; P<0.01: **; P value compared to vehicle.

As a mono-therapy, Compound 1 markedly reduced UACR, which was apparent one week after the start of treatment (FIG. 4). This inhibition persisted throughout the four-week study, with reductions of 72% and 57% at weeks three and four, respectively. As expected, RAAS blockade also significantly decreased the UACR. Notably, the addition of Compound 1 to the RAAS blockade achieved a further, statistically significant reduction in UACR, an additive effect consistent with two distinct mechanisms of action and similar results were obtained for UAER (Table 4).

TABLE 3

Reduction in UAER (mg/day) by Compound 1 alone, or in combination with RAAS blockade in 5/6 nephrectomy model

| RAAS blockade in 5/6 nephrectomy model | Week 1 | Week 2 | Week 3 |
| --- | --- | --- | --- |
| Vehicle | 26.82 | 17.21 | 39.55 |
| Compound 1 | 15.68, $p = 0.30$ | 6.72, $p = 0.07$ | 11.75, $p = 0.001$ |
| RAAS Blocker | 8.27, $p = 0.03$ | 3.62, $p = 0.03$ | 3.32, $p < 0.0001$ |
| Compound 1 + RAAS Blocker | 2.04, $p = 0.005$ | 1.45, $p = 0.009$ | 1.68, $p < 0.0001$ |
| No Treatment | 31.88 | 20.58 | 21.08 |

[1]Compound 1, 90 mg/kg
[2]RAAS Blocker, 5 mg/kg

TABLE 4

Reduction in UAER (mg/day) by combination of Compound 1 with RAAS blockade comparing with ET1/AT2 dual inhibitor in 5/6 nephrectomy model

| | Week 1 | Week 2 | Week 4 |
| --- | --- | --- | --- |
| Vehicle | 20.7 | 23.8 | 23.3 |
| Compound 1 | 7.1, $p = 0.07$ | 11.0, $p = 0.1$ | 2.8, $p = 0.02$ |
| RAAS Blocker | 9.4, $p = 0.27$ | 7.7, $p = 0.06$ | 1.7, $p = 0.02$ |
| Compound 1 + RAAS Blocker | 2.1, $p = 0.012$ | 1.95, $p = 0.002$ | 1.5, $p = 0.001$ |
| ET1/AT2 Dual Blocker | 2.6, $p = 0.036$ | 1.5, $p = 0.01$ | 1.15, $p = 0.001$ |

Figures 5A, 5B:
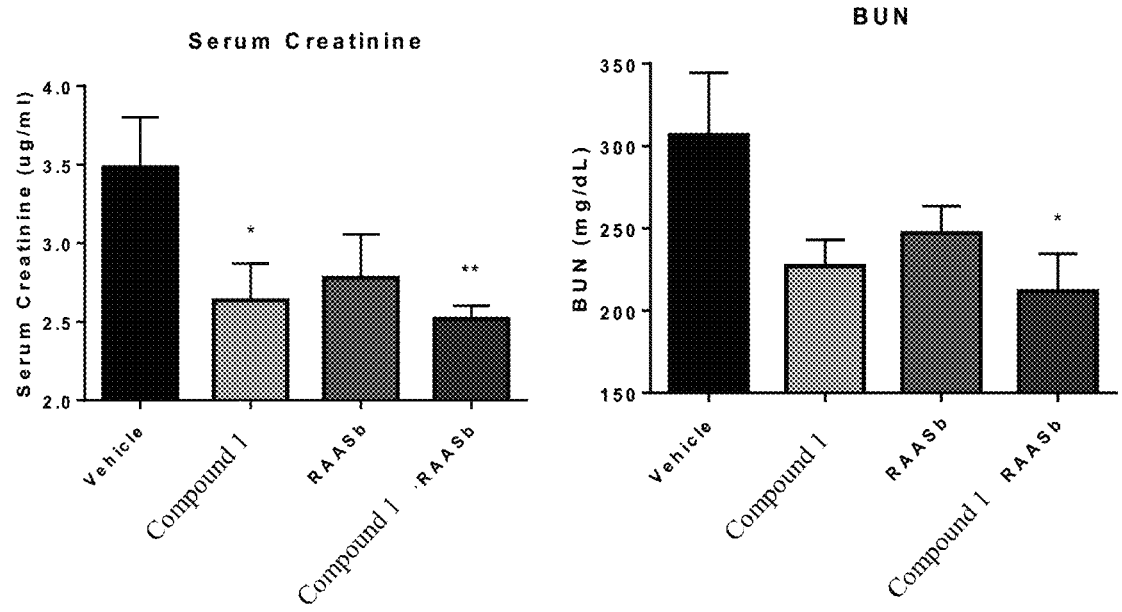
Figure 6A:
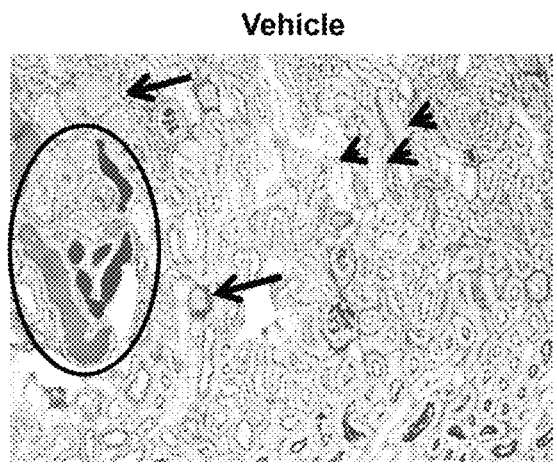
FIG. 6 Histological analysis of kidneys from the 5/6 nephrectomy model. The kidneys (8 animals/treated groups) were harvested 5 weeks after initiation of treatment, and fixed and stained as described in Methods. The kidneys were harvested 5 weeks after treatment began, and fixed and stained as described in Methods. Vehicle treatment is shown panel A; Compound 1 treatment is shown in panel B; RAAS blocker is shown in panel C; and combination of Compound 1 & RAAS blocker are shown in panel D. The magnification is 100×. The black cycle indicate areas of hyaline deposition, black arrows denote tubular collapse, and black arrowhead denotes tubular dilation.
Figure 6B:
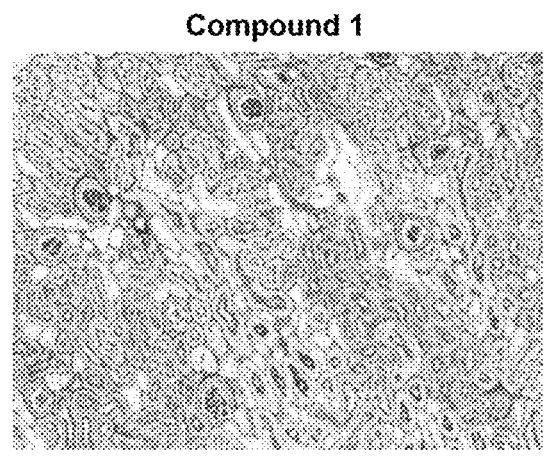
Figure 6C:
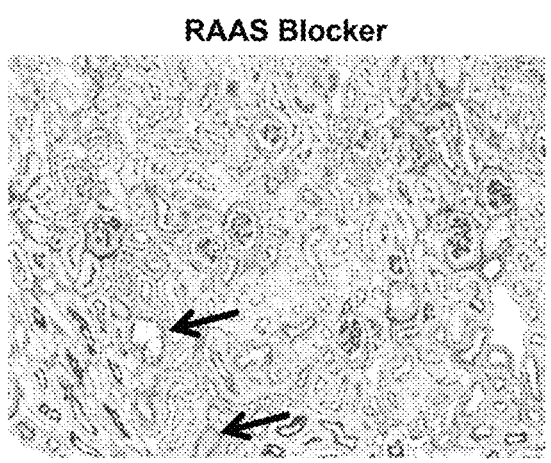
Figure 6D:
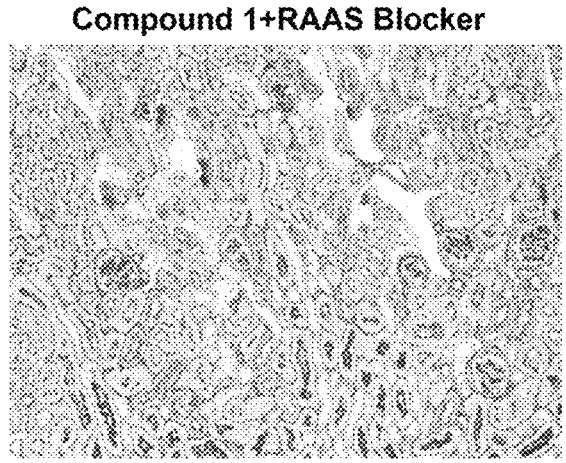
Figure 7A:
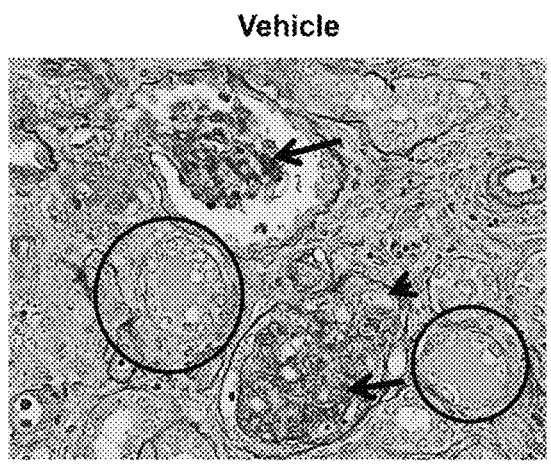
FIG. 7 Histological analysis of kidneys from the 5/6 nephrectomy model. The kidneys (8 animals/treated groups) were harvested 5 weeks after initiation of treatment, and fixed and stained as described in Methods. Vehicle treatment is shown in panel A; Compound 1 treatment is shown panel B; RAAS blocker is shown in panel C; and combination of Compound 1 & RAAS blocker are shown panel D. The magnification is 400×. The black cycle indicate areas of hyaline deposition, black arrows denote glomerular sclerosis, and black arrowhead denotes mesangial expansion.
Figure 7B:
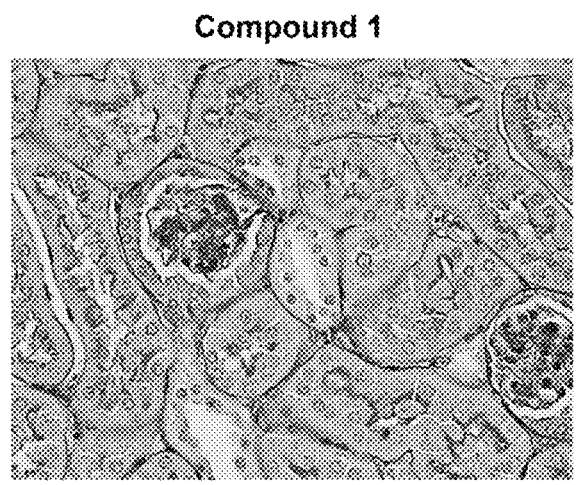
Figure 7C:
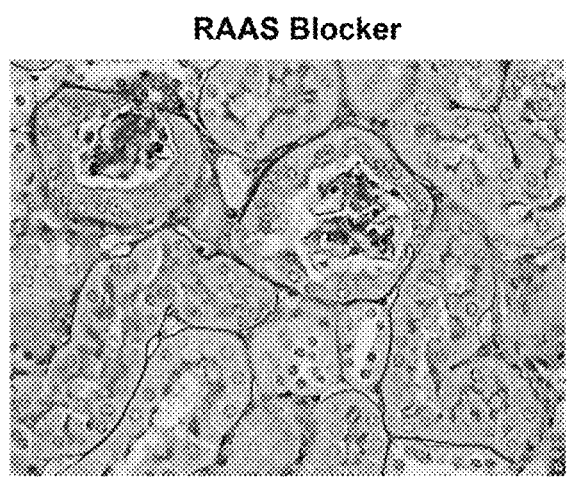
Figure 7D:
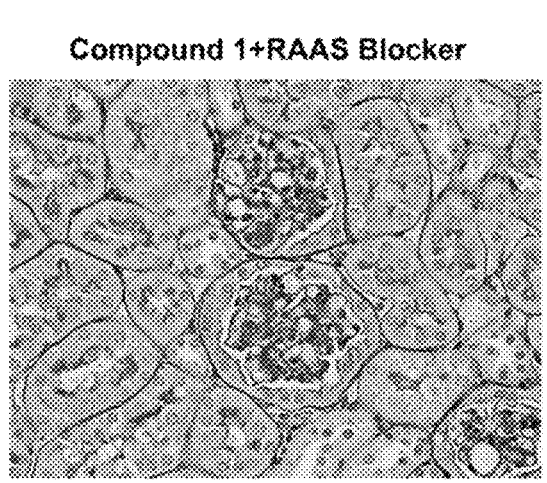

Compound 1 was associated with marked reductions in both creatinine and BUN with respect to vehicle control at the four-week time point (FIG. 5). The degree to which Compound 1 monotherapy reduced these parameters was greater or equal to that observed with RAAS blockade alone.

Example 6: Histological Analysis of Kidneys from the 5/6 Nephroctomy Model

Fixed kidney sections were obtained from 5/6 nephrectomized mice for pathology. The sections were stained and evaluated to determine whether the Compound 1-mediated improvements in renal function were associated with anatomical changes. As shown in FIG. 6 (100× magnification) reductions in tubular dilation and hyaline deposits (with respect to vehicle control) were evident in the kidney remnants from mice treated with Compound 1 alone or in combination with RAAS blockade. At higher magnification (400×), changes in the glomeruli were apparent, including decreased glomerular sclerosis, mesangial expansion, hyaline deposits and tubular collapse (FIG. 7).

Figure 8A:
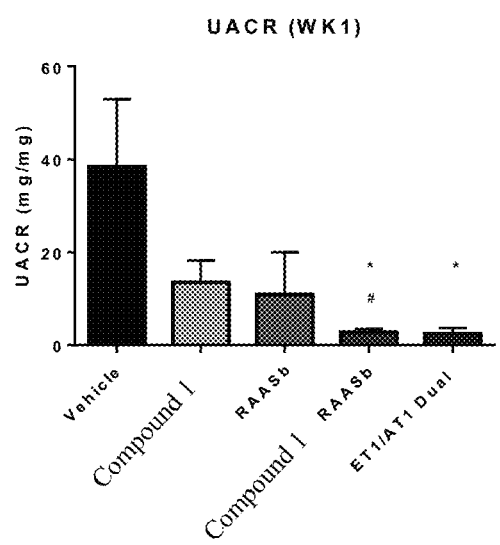
FIG. 8 Relative efficacy of CCR2, RAAS, and Endothelin Receptor Blockade in the 5/6 Nephrectomy Model. Mice underwent a 5/6 nephrectomy as described in Methods. Three weeks post-surgery the mice were randomized to the indicated groups for the study period of 4 weeks. Urine was collected for measurement of albumin and creatinine at week 1 (A) and week 4 (B), as described in Methods. Error bars represent standard error of the mean. N=10/group.
Figure 8B:
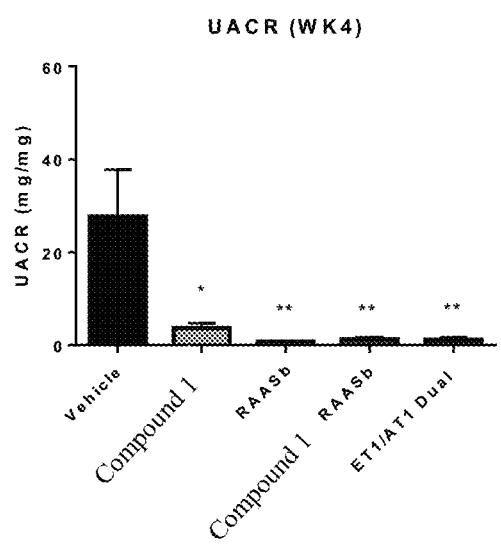

Example 7: Comparing CCR2 Inhibition to Endothelin Receptor Inhibition in the 5/6 Nephroctomy Model Endothelin has also been implicated in FSGS, and recent clinical trials have featured a dual-acting receptor antagonist for endothelin (A type) and angiotensin II receptors (Type 1) (Murugesan et al, 2005). We used the 5/6 nephrectomy model to determine how Compound 1 compared to this antagonist in providing renal protection in FSGS-like disease. The combination of Compound 1 and RAAS blockade was as effective as the combination of endothelin receptor inhibition plus RAAS blockade, as determined by both UACR and UAER (FIG. 8). Specifically, UACR was reduced by administration of Compound 1 alone (64.8%) or RAAS blocker alone (73.4%), at week one. Addition of the CCR2 antagonist to RAAS blockade further reduced the UACR (92.7% reduction vs vehicle, p=0.02; p<0.045 versus RAAS blockade alone), which was comparable to the combination of endothelin receptor plus RAAS blockade (93.5% reduction vs vehicle, p=0.019). These results indicate that CCR2 inhibition and endothelin receptor inhibition are equally effective when combined with RAAS blockade in this model of FSGS.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method of treating focal segmental glomerulosclerosis, said method comprising administering to a subject in need thereof a therapeutically effective amount of a CCR2 antagonist, wherein the CCR2 antagonist is a compound of Formula II (II)

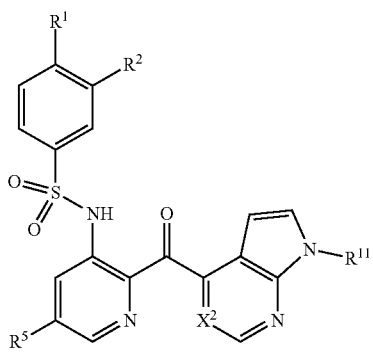

or a pharmaceutically acceptable form thereof,
wherein
R$^1$ and R$^2$ are each independently selected from the group consisting of hydrogen, halogen C$_{1-8}$ alkyl, CN, or C$_{1-8}$ haloalkyl, provided that at least one of R$^1$ or R$^2$ is other than hydrogen;
R$^6$ is halogen or C$_{1-8}$ alkyl;
X$^2$ is CR$^7$, N, or NO:
  R$^7$ is independently selected from the group consisting of hydrogen, halogen, C$_{1-8}$ alkyl, C$_{2-8}$ alkenyl, C$_{2-8}$ alkynyl, —CN, —NO$_2$, —OC(O)R$^8$, —CO$_2$R$^8$, —C(O)R$^8$, —C(O)NR$^9$R$^8$, —OC(O)NR$^9$R$^8$, —NR$^{10}$C(O)R$^8$, —NR$^{10}$C(O)NR$^9$R$^8$, —NR$^9$R$^8$, —NR$^{10}$CO$_2$R$^8$, —SR$^8$, —S(O)R$^8$, —S(O)$_2$R$^8$, —S(O)$_2$NR$^9$R$^8$, —NR$^{10}$S(O)$_2$R$^8$, C$_{6-10}$ aryl, 5- to 10-membered heteroaryl and 3- to 10-membered heterocyclyl;
  each R$^8$, R$^9$ and R$^{10}$ is independently selected from the group consisting of hydrogen, C$_{1-8}$ alkyl, C$_{2-8}$ alkenyl, C$_{2-8}$ alkynyl, aryl, or heteroaryl; or R$^9$ and R$^8$ or R$^{10}$ and R$^8$, together with the atom(s) to which they are attached, form a 5-, 6-, or 7-membered ring; and
R$^{11}$ is selected from the group consisting of hydrogen, C$_{1-8}$ alkyl, C$_{2-8}$ alkenyl, C$_{2-8}$ alkynyl, C$_{6-10}$ aryl, 5- to 10-membered heteroaryl and 3- to 10-membered heterocycle,
wherein the CCR2 antagonist is administered in combination with one or more additions therapeutic agents, the one or more additional therapeutic agents being a Renin-angiotensin-aldosterone (RAAS) blocker or an endothelin receptor antagonist.

2. The method of claim 1, wherein
R$^1$ and R$^2$ are each independently selected from the group consisting of halogen, C$_{1-8}$ alkyl, or C$_{1-8}$ haloalkyl, provided that at least one of R$^1$ or R$^2$ is other than hydrogen;
R$^5$ is halogen or C$_{1-8}$ alkyl;
X$^2$ is CR$^7$ or N;
R$^7$ is independently selected from the group consisting of hydrogen, halogen, C$_{1-8}$ alkyl, —CN, —NO$_2$, —OR$^8$, and —NR$^9$R$^8$;
R$^{11}$ is hydrogen or C$_{1-8}$ alkyl.

3. The method of claim 1, wherein
R$^1$ is halogen
R$^2$ C$_{1-8}$ haloalkyl;
R$^5$ is C$_{1-8}$ alkyl;
X$^2$ is CR$^7$ or N;
R$^7$ is independently selected from the group consisting of hydrogen, halogen, C$_{1-8}$ alkyl;

R$^{11}$ is hydrogen or C$_{1-8}$ alkyl.

4. The method of claim 1, wherein
R$^1$ is chloro
R$^2$ trifluoromethyl;
R$^5$ is methyl;
X$^2$ is CR$^7$ or N;
R$^7$ is independently selected from the group consisting of hydrogen, halogen, C$_{1-8}$ alkyl;
R$^{11}$ is hydrogen or C$_{1-8}$ alkyl.

5. The method of claim 1, wherein the compound of Formula II has the structure of Compound 1

(Compound 1)

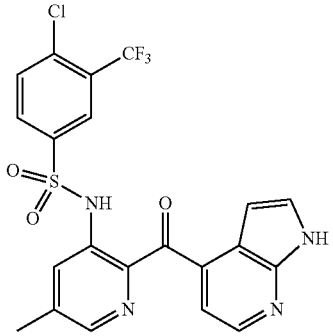

or a pharmaceutically acceptable form thereof.

6. The method of claim 1, wherein the compound of Formula II has the structure of Compound 2

(Compound 2)

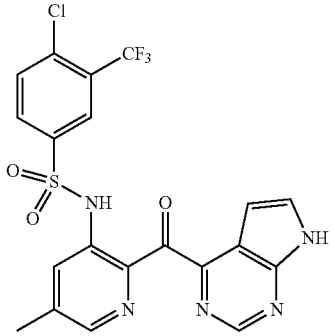

or a pharmaceutically acceptable form thereof.

7. The method of claim 1, wherein the CCR2 antagonist is administered daily.

8. The method of claim 1, wherein administration of the CCR2 antagonist to the subject in need thereof reduces a urine albumin-to-creatinine ratio in said subject.

9. The method of claim 8, wherein the urine album in-to-creatinine ratio in said subject is reduced by at least 20% after 3 weeks of administering the CCR2 antagonist as compared to the albumin to creatinine ratio in said subject prior to treatment.

10. The method of claim 8, wherein the urine album in-to-creatinine ratio in said subject is reduced by at least 30% after 3 weeks of administering the CCR2 antagonist as compared to the albumin to creatinine ratio in said subject prior to treatment.

11. The method of claim 8, wherein the urine albumin-to-creatinine ratio in said subject is reduced by at least 40% after 3 weeks of administering the CCR2 antagonist as compared to the albumin to creatinine ratio in said subject prior to treatment.

12. The method of claim 8, wherein the urine albumin-to-creatinine ratio in said subject is reduced by at least 50% after 3 weeks of administering the CCR2 antagonist as compared to the albumin to creatinine ratio in said subject prior to treatment.

13. The method of claim 8, wherein the urine albumin-to-creatinine ratio in said subject is reduced by at least 60% after 3 weeks of administering the CCR2 antagonist as compared to the albumin to creatinine ratio in said subject prior to treatment.

14. The method of claim 1, wherein the CCR2 antagonist is a selective CCR2 antagonist.

15. The method of claim 1, wherein the additional therapeutic agent is a Renin-angiotensin-aldosterone (RAAS) blocker.

16. The method of claim 15, wherein the RAAS blocker is a renin inhibitor.

17. The method of claim 16, wherein the renin inhibitor is selected from the group consisting of aliskiren, remikiren, H-142, SPP635, SPP1148, SPP676, and SPP1234.

18. The method of claim 15, wherein the RAAS blocker is an ACE inhibitor.

19. The method of claim 18, wherein the ACE inhibitor is enazepril, captopril, enalapril, fosinopril, lisinopril, perindopril, quinapril, rampipril, and trandolapril.

20. The method of claim 15, wherein the RAAS blocker an angiotensin receptor blocker (ARB).

21. The method of claim 20, wherein the ARB is selected from the group consisting of sparsentan, eprosartan, candesartan, irbesartan, losartan, olmesartan, telmisartan, valsartan, CGP-42112A, DuP753, saralasin, and sarthran.

22. The method of claim 20, wherein the ARB is selected from the group consisting of eprosartan, candesartan, irbesartan, losartan, olmesartan, telmisartan, valsartan, CGP-42112A, DuP753, saralasin, and sarthran.

23. The method of claim 20, wherein the ARB is candesartan.

24. The method of claim 1, wherein the additional therapeutic agent is an endothelin receptor antagonist.

25. The method of claim 24, wherein the endothelin receptor antagonist is selected from the group consisting of sparsentan, bosentan, macitentan, ambrisentan, sitazentan, aprocitentan, and artasentan.

26. The method of claim 24, wherein the endothelin receptor antagonist is sparsentan.

* * * * *

UNITED STATES PATENT AND TRADEMARK OFFICE
CERTIFICATE OF CORRECTION

PATENT NO. : 10,758,540 B2  
APPLICATION NO. : 16/156608  
DATED : September 1, 2020  
INVENTOR(S) : Zhenhua Miao et al.

Page 1 of 1

It is certified that error appears in the above-identified patent and that said Letters Patent is hereby corrected as shown below:

In the Claims

In Claim 1, Column 21, Line 23, please delete "$R^6$" and insert in place thereof --$R^5$--

Signed and Sealed this  
Fifteenth Day of March, 2022

Drew Hirshfeld  
*Performing the Functions and Duties of the*  
*Under Secretary of Commerce for Intellectual Property and*  
*Director of the United States Patent and Trademark Office*